United States Patent [19]

Labrie et al.

[11] Patent Number: 6,110,906

[45] Date of Patent: Aug. 29, 2000

[54] ANDROGEN DERIVATIVES FOR USE IN THE INHIBITION OF SEX STEROID ACTIVITY

[75] Inventors: Fernand Labrie; Yves Mérand, both of Ste-Foy, Canada

[73] Assignee: Endorecherche, Inc., Quebec, Canada

[21] Appl. No.: 08/279,262

[22] Filed: Jul. 21, 1994

Related U.S. Application Data

[63] Continuation of application No. 07/972,883, Nov. 5, 1992, abandoned, which is a continuation of application No. 07/376,696, Jul. 7, 1989, which is a continuation-in-part of application No. 07/322,154, Mar. 10, 1989.

[51] Int. Cl.$^7$ .................. C07J 1/00; C07J 5/00; A61K 31/565; A61K 31/57
[52] U.S. Cl. ................ 514/163; 514/182; 552/623
[58] Field of Search ....................... 514/163, 182; 552/623

[56] References Cited

U.S. PATENT DOCUMENTS

| | | | |
|---|---|---|---|
| 3,001,988 | 9/1961 | Nysted | 552/522 |
| 3,300,523 | 1/1967 | Brown | 552/505 |
| 3,975,413 | 8/1976 | Pierdet et al. | 260/397.1 |
| 3,995,060 | 11/1976 | Neri et al. | 514/600 |
| 4,024,248 | 5/1977 | Koning et al. | 514/15 |
| 4,039,669 | 8/1977 | Beyler et al. | 424/243 |
| 4,055,641 | 10/1977 | Benson et al. | 514/177 |
| 4,100,274 | 7/1978 | Dutta et al. | 514/15 |
| 4,118,483 | 10/1978 | Konig et al. | 514/15 |
| 4,139,638 | 2/1979 | Neri et al. | 514/625 |
| 4,161,540 | 7/1979 | Neri et al. | 514/625 |
| 4,191,759 | 3/1980 | Johnston et al. | 514/177 |
| 4,235,893 | 11/1980 | Brodie | 552/600 |
| 4,329,364 | 5/1982 | Neri et al. | 930/20 |
| 4,386,080 | 5/1983 | Crossley et al. | 514/522 |
| 4,481,190 | 11/1984 | Nestor et al. | 514/15 |
| 4,547,493 | 10/1985 | Teutsch et al. | 514/179 |
| 4,634,696 | 1/1987 | Teutsch et al. | 514/169 |
| 4,659,516 | 4/1987 | Bowler et al. | 260/397.5 |
| 4,659,695 | 4/1987 | Labrie | 514/800 |
| 4,732,912 | 3/1988 | Pilgrim et al. | 514/510 |
| 4,751,240 | 6/1988 | Bowler et al. | 514/510 |
| 4,760,053 | 7/1988 | Labrie | 514/177 |
| 4,760,061 | 7/1988 | Edwards et al. | 514/211 |
| 4,904,661 | 2/1990 | Pilgrim et al. | 514/237.5 |
| 5,021,414 | 6/1991 | Pilgrim et al. | 514/231.5 |
| 5,364,847 | 11/1994 | Labrie et al. | 514/182 |

FOREIGN PATENT DOCUMENTS

| | | | |
|---|---|---|---|
| 10669/88 | 7/1988 | Australia . | |
| 10778/88 | 8/1988 | Australia . | |
| 31569/89 | 9/1989 | Australia . | |
| 58481 | 8/1982 | European Pat. Off. . | |
| 163416 | 12/1985 | European Pat. Off. . | |
| 0285383 | 3/1988 | European Pat. Off. | 546/77 |
| 7022461 | 6/1970 | France | 514/453 |
| 1917087 | 11/1969 | Germany . | |
| 2529969 | 1/1976 | Germany . | |
| 3339295 | 5/1984 | Germany . | |
| 55-013273 | 3/1980 | Japan . | |
| 137542 | 9/1967 | New Zealand . | |
| 123341 | 9/1970 | New Zealand . | |
| 182661 | 7/1979 | New Zealand . | |
| 206745 | 1/1984 | New Zealand . | |
| 207413 | 11/1984 | New Zealand . | |
| 213652 | 9/1985 | New Zealand . | |
| 222883 | 12/1987 | New Zealand . | |
| 208441 | 1/1988 | New Zealand . | |
| 214798 | 9/1988 | New Zealand . | |
| 214998 | 6/1989 | New Zealand . | |
| 222103 | 8/1989 | New Zealand . | |
| 223262 | 8/1989 | New Zealand . | |
| 1081494 | 8/1967 | United Kingdom . | |
| 2025422 | 1/1980 | United Kingdom . | |
| 9100732 | 1/1991 | WIPO . | |

OTHER PUBLICATIONS

Salman, et al., $^{125}$I–Ligand For Progesterone Receptor: 17α–(6'–Iodohex–1'–ynyl)–19–nortestosterone, *J Steroid Biochem* vol. 33, No. 1, pp 25–31, 1989.
Green, et al., *Nature* 320: 134, 1986.
Luthy, etal J Steroidal Biochem. 31(5)845–52 1988.
Plante, J. Steroidal Biochem. 31(1)61–64, 1988.
Voight, etal, EMBO 1973 92(4)pp.1216–22.
Green, etal, Nature 320(13) Mar. 1986 pp.134–139.
Lubahn, etal Science, 1988 pp. 327–330.
Lubahn, etal Proc. Natl. Acad Sci. USA 86 9534–9538 Dec. 1989.
Tora, etal, EMBO 8(7) 1981–1986, 1989.
Doorenbos, etal J.Pharm. Sciences 62(4),1973 pp. 638 to 640.
Doorenbos, etal J. Pharm. Sciences 60(18) 1971 pp. 1234–1235.
Mayfeh, etal Steroids 14:3, 1969 pp. 269 to 283.
Doorenbos, etal J. Pharm. Sciences 63(4) 1974 pp. 620 to 622.
Auchus, etal, Biochemistry 1986 257295–7300 Riess.
Schwartz, Organic Synthesis Collective vol. 3.
Cooke—Jr. Tetrahedron Letters 22 pp. 1923–1986, 1973.
Gibson. etal Angew Chem. Int.Ed. 7(1968)No.12, pp 919–930.
Neri, etal J. Steroidal Biochem. 1975(6) pp 815–819.
Chang, etal Biochemistry 1982 27–410 2–4109.
Gyortii, etal J. Steroidal Biochem. 25(3) 355–358, 1986.
Macaulay,etal J. Steroidal Biochem 26(5)535–538 1987.
Grunwell,etal, Steroids 27(6) 1976 pp. 759 to 771.
Chen, etal J.Biol.Chem 250(19), 1975 pp. 7682–7686.
Rauchee, etal J.Org.Chem, 1981 46 3558–3559.

(List continued on next page.)

*Primary Examiner*—Mukund J. Shah
*Assistant Examiner*—Bruck Kifle
*Attorney, Agent, or Firm*—Ostrolenk, Faber, Gerb & Soffen, LLP

[57] ABSTRACT

Methods for treating sex steroid-dependent diseases by inhibiting sex steroid activity include administration of novel compounds which include an androgenic nucleus substituted at a ring carbon with at least one substituent specified herein. Such compounds may function by inhibiting sex steroid synthesis (both estrogen and androgen synthesis) and/or by antagonistically blocking androgen receptors.

18 Claims, 3 Drawing Sheets

OTHER PUBLICATIONS

Weiss, etal Angew Chem.Int.Ed. 12(1973)No. 10 p. 841.

Bull,etal Chem Soc. Chem Commun 1986 p. 451–453.

Wang, etal, Can. J. Chem 65, 2727 1987.

Salman,etal J.Steroidal Biochem. 26(3) 383–391, 1987.

Jordan,etal, Endocrinology, 124(4), 1989 pp.1717 to 1726.

R.J. Donnelly, "Continuous Subcutaneous Administration of 'Zoladex' (ICI 118,630—An LH–RH Analogue) to Patients with advanced Prostatic Cancer", ICI Pharmaceuticals Division, Macclesfield, U.K.

Beardwell, C.G., Hindley, A.C., Wilkinson, P.M., Todd, I.D., Pibeiro, G.G., Bu'Lock, D. (1983) Trilostane in the treatment of advanced breast cancer. Cancer Chemother. Pharmacol. 10, No. 3, 158–160.

Brooks, J.R., Berman, D., Glitzer, M.S., Gordon, L.R., Primka, R.L., Reynolds, G.F., Rasmusson, G.H. (1982) Effect on a new 5 alpha–reductase inhibitor on size, histologic, characteristics and androgen concentration of a canine prostate. The Prostate, 3, No. 1, 35–44.

Bruchovsky, N., Wilson, J.D. (1968) The converstion of testosterone to 5α–androstan–17β–01–3–one by rat prostate in vivo and in vitro J. Biol. Chem. 243, No. 8, 2012–2021.

Coy, D.H., Horvath, A., Nekola, M.F., Coy, E.J., Erchegyi, J., Schally, A.V. (1982) Peptide antagonists of LH–RH: large increases in antiovulatory activities produced by basic D–amino acids in he six position. Endocrinology, 110, 1445–1447.

Debruyne, F.M.J. (1988) The case for LHRH agonists. In: Bailliere's Clinical Oncology International Practice and Research, (Furr, B.J.A., Denis, S., eds). Bailliere's Tindall, pp.559–570.

Labrie, F., Dupont, A., Belanger, A. and members of the Laval University Prostate Cancer Program (1984) Dramatic response to a new antihormonal treatment for prostate cancer. 7th International Congress of Endocrinology 1984, p. 98.

Lambert, A., Frost, J., Mitchell, R., Robertson, W.R. (1986) On the assessment of the in vivo biopotency and site(s) of action of drug affecting adrenal steroidogenesis. Ann. Clin. Biochem., 23, 225–229.

Potts, G.O., Creanage, J.E., Handomg, H.R., Schane, H.P. (1978) Triostane, an orally active inhibitor of steroid biosynthesis. Steroids, 32, No. 2, 257–267.

Wilson, J. (1975) Metabolism of testicular androgens. In: Handbook of Physiology: a critical, comprehensive presentation of physiological knowledge and concepts. Section 7, Endocrinology; vol. V, Male reproductive system, (Hamilton, D. Greep, R.O., eds). Washington, DC: American Physiology Society, pp. 491–508.

Robinson, D.T., Earnshaw, R.J., Mitchell, R., Powles, P., Andrews, R.S., Robertson, W.R. (1984) The bioavailability and metabolism of trisostane in normal subjects, a comparative study using high pressure liquid chromatographic and quantitative cytochemical assays. J. Steroid Biochem., 21, No. 5, 601–605.

Habenicht, U.F., Schwarz, K., Neumann, F., El Etreby, M.F. (1987) Induction of estrogen–related hyperplasic changes in the prostate of the cynomolgus monkey (*macaca fascicularis*) by androstenedione and its antagonization by the aromatase inhibitor 1–methyl–androsta–I,4–diene–3, 17–dione. The Prostate, 11, 313–326.

DeKlerk, D.P., Human, H.J., De Klerk, J.N. (1985) The effect of 5α–androstane–3α, 17β–diol and 17β–estradiol on the adult and immature chacma baboon prostate. The Prostate, 7, 1–12.

Coy, D.H., Vilchez–Martinez, J.S., Co, E.J., Schally, A.V. (1976) Analogs of luteinizing hormone–releasing hormone with increased biologival activity produced by D–amino acid substitutions in position 6. J.Med. Chem., 19, No. 3, 423–425.

Wenderoth, U.K., George, F.W., Wilson, J.D. (1983) The effect of a 5α–reductase inhibition on androgen–mediated growth of the dog prostate. Endocrinology, 113, No. 2, 569–573.

McConnell, J.D., Wilson, J.D., George, F.W., Geller, J., Walsh, P.C., Ewing, L. L., Isaacs, J., Stoner, E. (1989) An inhibitor of 5α–reductase, MK–906, suppresses prostatic dihydrotestosterone in men with begign prostatic hyperplasia. AUA Eighty–fourth Annual Meeting (Dallas, May 7–11). The Journal of Urology, 141, 239A, No. 280.

Stoner, E. (1989) Lecture on the role of 5–alpha–reductase inhibitor in BPH. AUA Today, No. Nov./Dec.

Toomey, R.E., Goode, R.L. Petrow, V., Neubauer, B.L. (1989) An in vivo assay for conversion of testosterone (T) to dihydrotestosterone (DHT) by prostatic steroid 5–alpha–reductase and comparison of two inhibitors. 71st Annual Meeting of the Endocrine Society Meeting (Seattle, Jun. 21–24). No. 1226, p. 329.

Labrie, C. Cusan, L., Plante, M. Lapointe, S., Labrie, F. (1987) Analysis ofthe androgenic activity of synthetic "progestins" currently used for the treatment of prostate cancer. J. Steroid Biochem., 28, No. 4, 379–384.

Simard, J., Labrie, C., Hubert, J.F., Labrie, F. (1988) Modulation by sex steroids and [D–Trp6, des–gly–NH210] luteinizing hormone (LH)–releasing hormone ethylamide of α–subunit and LHβ messenger ribonucleic acid levels in the rat anterior pituitary gland. Molecular Endocrinology, 2, No. 9, 775–784.

Moore, R.J., Gazak, J.M., Wilson, J.D. (1979) Regulation of cytoplasmic dihydrotestosterone binding in dog prostate by 17β–estradiol. J. Clin. Invest., 63, 351–357.

Brooks, J.R., Baptista, E.M., Berman, C., Ham, E.A., Hichens, M., Johnston, D. B.R., Primka, R.L., Rasmuson, G.H., Reynolds, G.F. Schmitt, S.M., Arth, G. E. (1981) Response of rat ventral prostate to a new and novel 5α–reductase inhibitor. Endocrinology, 109, No. 2, 830–836.

Geller, J., Franson, A.V. (1989) Effect of MK906 on prostate tissue, androgens and prostate specific antigen. 71st Annular Meeting of the Endocrine Society (Seattle, Jun. 21–24), No. 1640, p. 432.

Gormley, G.J., Rittmaster, R.S., Gregg, H., Lasseter, K.C., Ferguson, D., Stoner, E. (1989) Dose response effect on an orally active 5–alpha–reductase inhibitor (MK 906 in man. 71st Annual Meeting of the Endocrine Society (Seattle, Jun. 21–24). No. 1225, p. 329.

Wagner, R.K., Schulze, K.H., Jungblut, P.W. (1975) Estrogen and androgen receptor in human prostate and prostatic tumor tissue. Acta Endocr. (Kbh), Suppl. 193, 52 (abst).

Swaneck, G.E. Alvarez, J.M. Sufrin, G. (1982) Multiple species of estrogen binding sites in the nuclear fraction of the rat prostate. Biochemical Biophysical Research Communications, 106, No. 4, 1441–1447.

Petrow, V., Padilla, G.M. Kendle, K. Tantawi, A. (1982) Inhibition of prostatic growth in rats by 6–methylne–4–pregnene–3,20–dione. J. Endocr., 95, 311–313.

Kadohma, N., Wakisaka, M., Kim, U., Karr, J.P., Murphy, G.P., Sandberg, A.A. (1985) Retardation of prostate tumor progression in the noble rat by 4–methyl–4–aza–steroidal inhibitors of 5α–reductase. J. Natl. Cancer Inst., 74, No. 2, 475–486.

Earnshaw, R.J., Mitchell, R., Robertson, W.R. (1984) A cytochemical section bioassay fro plasma trilostane: an orally active inhibitor of 3α–hydroxysteroid dehydrogenase activity. Clin. Invest., 21, 13–21.

Corbin, A., Bex, F.J., Jones, R.C. (1984) Comparison of LHRH agonist (AG) and antagonist (ANT): antifertility and therapeutic developments. 7th International Congress of Endocrinology (Quebec, Jul. 1–7). J. steroid Biochem., 20 (6B), 1369, No. A9.

Dutta, A.S., Furr, B.J.A., Giles, M.B., Valcaccia, B. (1978) Synthesis and biological activity of highly active α–aza analogues of luliberin. J. Med. Chem., 21, No. 10, 1018–1024.

Erchegyi, J., Coy, D.H., Nekola, M.V., Coy, E.J. Schally, A.V., Mezo, I., Teplan, I. (1981) Luteinizing hormone–releasing hormone analogs with increased anti–ovulatory activity. Biochemical and Biophysical Research Communications 100, No. 3, 915–920.

Nestor, Jr. J.J., Ho, T.L., Tahilramani, R., McRae, G.I. Vickery, B.H. (1984) Long–acting LHRH agonists and antagonists. 7th International Congress of Endocrinology (Quebec, Jul. 1–7). J. Steroid Biochem., 20 (6B), 1366, No. A3.

Nestor, J.J. (1984) Development of agonistic LHRH analogs. In: LHRH and its analogs, contraceptive and therapeutic applications, (Vickery, B.H., Nestor, J.J. Hafez, E.S.E., eds). Lancaster, England, MTP Press Limited. pp. 3–10.

Williams, C.J., Barley, V., Blackledge, G. Hutcheon, A., Kaye, S., Smith, D., Keen C., Webster, D.J.T., Rowland, C., Tyrrell, C. (1987) Multicenter study of trilostane: a new hormonal agent in advanced postmenopausal breast cancer. Cancer Treatment Reports, 71, No. 12, 1197–1201.

Chan, W.K., Fong, C.Y., Tiong, H.H., Tan, C. H. (1987) The inhibition of 3βHSD activity in porcine granulosa cells by 4–MA, a potent 5–α–reductase inhibitor. Biochemical Biophysical Research Communication, 144, No. 1, 166–171.

Taylor, M.J. (1987) Inhibition of progesterone secretion by a 3β–hydroxysteroid dehydrogenase inhibitor in pregnant goats. J. Endocr., 113, 489–493.

Rivier, J., Varga, J. Rivier, C., Perrin, M., Struthers, S., Hagler, A., Vale, W. (1984) Structurally constrained LHRH analogs. 7th International Congress of Endocrinology (Quebec, Jul. 1–7), J. Steroid Biochem., 20 (6B), 1365, No. A1.

Labrie, et al., "LHRH Agonists and Antiandrogens in Prostate Cancer", pp. 257–199, Ratliff, T.L. and Catalona, W.J. (eds), Genitourinary Cancer. ISBN 0–89838–830–9, 1987, Martinus Nijhoff Publishers, Boston.

N. Faure, et al., "Buserelin therapy for prostatic carcinoma", LHRH and Its Analogs, pp. 337–349.

P.C. Walsh, et al., "The Induction of Prostatic Hypertrophy in the Dog with Androstanediol", The Journal of Clinical Investigation, vol. 57, Apr. 1976, pp. 1093–1097.

J.R. Brooks, et al. "Biological Activities of a New Steroidal Inhibitor of Δ⁴–5α–Reductase (41309), Proceedings of the Society for Experimental Biology and Medicine", 169, 67–73 (1982).

F.W. George, et al., "The Effect of A 5–α–Reductase Inhibitor on Androgen Physiology in the Prepubertal Male Rat", 1165, Department of Cell Biology and Anatomy, University of Texas Southwestern Medical Center, Dallas, TX 75235.

J. Imperato–McGinley, et al., "Comparison of Plasma and Urinary C19 and C21 5α–Metabolites in Subjects Treated With the 5α–Reductase Inhibitor MK906 and Male Pseudohermaphrodites with Inherited 5α–Reductase Deficiency", 1639, Cornell Univ. Med, Coll., NY, NY 10021.

J.S. Tenover, et al., "Effects of 24–Week Administration of a 5α–Alpha Reductase Inhibitor (MK–906) on Serum Levels of Testosterone (T), Free T, and Gonadotropins in Men", 583, Department of Medicine, University of Washington, Seattle, WA 98103.

T. Liang, et al., "Binding of a 4–Methyl–4–Aza–Steroid to 5α=Reductase of Rat Liver and Prostate Microsomes", Endocrinology, vol. 112, No. 4, pp. 1460–1468.

T. Liang, et al., "4–Azasteroidal 5α–Reductase Inhibitors with Affinity for the Androgen Receptor", The Journal of Biological chemistry, vol. 259, No. 2, pp. 734–739.

J.R. Brooks, et al. "5α–Reductase Inhibitory and Anti-Androgenic Activities of Some 4–Azasteroids in the Rat", Steroids 47/1, Jan. 1986 (1–19).

J. Rivier, et al., LHRH Analogs as Antiovulatory Agents, pp. 11–22.

J.J. Nestor, Jr. et al. LHRH Agonists and Antagonists Containing Very Hydrophobic Amino Acids, pp. 23–33.

F.M.J. Debruyne, "The Case for LHRH Agonists", Bailliere's Clinical Oncology, vol. 2, No. 3, pp. 559–570, Nov. 1988.

Salman et al., J. steroid. Biochem vol. 26, No. 3 pp. 383–391, 1987.

K.B. Sharpless, et al., *Tetrahedron Letters*, 1979 (1973).

J. Riest, *Bull. Soc. Chim.* 18 (1956).

J. Fujimoto, *J. Pharm. Soc. Jap*, 87:270 (1967).

M. Toth, et al. (1982) *J. Steroid Biochem* 17:653–660.

Junkmann, K. (1957) "Long–Acting Steroids In Reproduction", *Recent Progr. Horm. Res.*, 13:1389–1427, Academic Press, New York.

Weinbauer, G.F., et al. (1986) *Acta Endocrinologica* 113: 128–132.

Séguin, et al. *Mol. Cell. Endocrinol.*, 21, 37–41, 1981.

Neumann, et al., *In: Clinics in Oncology*, vol. 1, pp. 41–64, 1982, Ed. B.J.A. Furr, Eastbourne; W.B. Saunders.

Simard, et al., *Mol. Cell, Endocrinol.*, 44, 261–270, 1986.

Poyet and Labrie, *Mol. Cell. Endocrinol.*, 42, 283–288, 1985.

Furr, et al. *J. Endocr.*, 113, R7–R9, 1987.

Labrie, et al., *Important Advances in Oncology*, Eds. V.T. De Vita, et al. J.B. Lippincott Company, Philadelphia, pp. 193–217, 1985.

Wakeling, A.E., et al. *J. Endocr.*, 112, R7–R10, 1987.

Wakeling, A.E., et al. *J. Steroid Biochem.*, 30, 141–147.

Y.M. Bhatnager, et al. *Biol. Chem.* 253, 811–815, 1978.

C.C. Chin, et al. *J. Biol. Chem.*, 255, 3660–3664, 1980.

J.L. Thomas, et al. *J. Biol. Chem.*, 258, 1587–1590, 1983.

B. Tobias, et al. *J. Biol. Chem.*, 257, 2783–2786, 1982.

Thomas, J.L., et al. *J. Biol. Chem.*, 258, 11500, 1983.

Labrie, C., et al. *Endocrinology* 123: 1412–1417, 1988.

Plante, et al., *J. Steroid Biochem.*, 31: 64–67, 1988.

Musto, et al., A Novel Affinity Column for Isolation of Asnrogen Binding Protein... (1977), pp. 147–157.

Synthesis and activity as androgens... (1982), pp. 603–614.

De Larminat, et al., Synthesis and evaluation of immobilized androgens for affinity chromatography... (1984), pp. 123–140.

Gohring, et al., A giant step for mankind ?(1989), World Patent Information, vol. 11, No. 1, pp. 5–10.

ANDROGEN DERIVATIVES FOR USE IN THE INHIBITION OF SEX STEROID ACTIVITY

RELATED APPLICATION

This application is Continuation of application Ser. No. 07/972,883 filed on Nov. 5, 1992, now abandoned, which is in turn a Continuation of application Ser. No. 07/376,696 filed on Jul. 7, 1989, which is in turn a Continuation-in part of U.S. patent application Ser. No. 07/322,154 filed Mar. 10, 1989, the disclosure of which is incorporated herein by reference.

BACKGROUND OF THE INVENTION

This invention relates to novel inhibitors of sex steroid activity such as antiandrogen compounds having effective antagonistic capability while substantially lacking agonistic effects. More particularly, certain preferred embodiments of the invention relate to certain dihydrotestosterone analogs which have high affinity for androgen receptors but do not activate such receptors and/or which inhibit the production of sex steroids or their precursors.

BRIEF DESCRIPTION OF THE PRIOR ART

During the treatment of certain sex steroid-dependent diseases, it is important to greatly reduce or, if possible, eliminate certain sex steroid-induced effects. For this purpose, it is desirable both to block receptor sites stimulated by sex steroids and also to reduce the amount of sex steroid available to act at these sites. For example, alternative or concurrent therapy to administration of antiandrogens could involve attempts to block the production of androgens such that none is available to activate receptor sites. However, prior art methods for blocking androgen production and/or reducing androgen concentration insufficiently inhibit androgen-induced functions. Moreover, it is possible that even in the total absence of androgen, unoccupied androgen receptors may be biologically active. Hence, antiandrogens may produce greater therapeutic results than therapy which only inhibits androgen production.

Antiandrogens may have a significant therapeutic effect in slowing or stopping the progress of androgen-dependent diseases such as prostate cancer. Known antiandrogens such as cyproterone acetate, spironolactone, flutamide and anandron have been used in clinical studies of androgen-responsive diseases. The nonsteroidal compounds flutamide and anandron are pure effective antiandrogens (i.e., do not activate androgen receptors), but cause an increase in serum concentration of luteinizing hormone (LH) and testosterone (Neri and Peets, J. Steroid Biochem. 6, 815–819, 1975; Séguin et al., Mol. Cell. Endocrinol. 21, 37–41, 1981; Neumann et Jacobi, In: Clinics in Oncology, Vol. 1, pp. 41–64, 1982, Ed. B. J. A. Furr, Eastbourne; W. B. Saunders). Moreover, nonsteroidal antiandrogens of the prior art possess a relatively low affinity for the androgen receptor (Simard et al., Mol. Cell. Endocrinol. 44, 261–270, 1986). On the other hand, steroidal antiandrogens (i.e., cyproterone acetate and spironolactone), while having better receptor affinity, may possess intrinsic androgenic activity, thus undesirably functioning as agonists (Poyet and Labrie, Mol. Cell. Endocrinol. 42, 283–288, 1985; Labrie, C. et al., J. Steroid Biochem. 28, 379–384, 1987; Luthy et al., J. Steroid Biochem. 31, 845–852, 1988; Plante et al., J. Steroid Biochem. 31, 61–64, 1988).

There is, therefore, a need in the art for antiandrogens which more effectively block peripheric androgen receptors with neither activity on central nervous system nor progestational, nor intrinsic androgenic or glucocorticoid activity.

Certain nonsteroidal compounds which are stated to have antiandrogenic effect are described by Furr et al., J. Endocr. 113, R7–R9, 1987.

In U.S. Pat. No. 4,329,364, it is disclosed that the antiandrogen, 4'-nitro-3'-trifluoromethyl isobutyranilide may be used for treatment of prostatic cancer.

F. Labrie et al., The Prostate 4, 579–594, 1983, disclose that use of a combination therapy of an LHRH agonist (Buserelin) and an antiandrogen (Anandron) to treat advanced prostate cancer in previously untreated patients affects simultaneous elimination of androgens of both testicular and adrenal origin.

F. Labrie et al., J. Steroid Biochem. 19, 99–1007, 1983, disclose the treatment of prostate cancer by the combined administration of an LHRH agonist and an antiandrogen. Labrie et al. disclose animal and clinical data in support of the proposition that the combined LHRH/anti-androgen treatment neutralizes the stimulatory influence of all androgens on the development and growth of androgen-dependent prostatic cancer.

In U.S. Pat. No. 4,659,695, a method of treatment of prostate cancer is disclosed for susceptible male animals including humans whose testicular hormonal secretions are blocked by surgical or chemical means, e.g., by use of an LHRH agonist, e.g., [D-Trp$^6$, des-Gly-NH$_2^{10}$]LHRH ethylamide. The treatment includes administering an antiandrogen, e.g., flutamide in association with at least one inhibitor of sex steroid biosynthesis, e.g., aminoglutethimide and/or ketoconazole.

F. Labrie et al., in: Genitourinary Cancer, eds. T. L. Ratliff and W. J. Catalona, Martinus Nijhoff Publishers, Boston, pp. 157–200, 1987 and in: Important Advances in Oncology, eds. V. T. De Vita, S. Hellman and S. A. Rosenberg, J. B. Lippincott Company, Philadelphia, pp. 193–217, 1985 describe the role of peripheral formation of androgens from inactive adrenal steroid precursors and the need to use a pure antiandrogen for the treatment of androgen-sensitive diseases.

C. Labrie et al., J. Steroid Biochem. 28, 379–384, 1987, describe the potent stimulatory effect of the adrenal precursors dehydroepiandrosterone and androstenedione on the growth of the prostate in the rat.

U.S. Pat. No. 4,472,382 discloses a method of treating prostate cancer using the combination of an antiandrogen and an LHRH agonist.

In U.S. Pat. No. 4,386,080, it is disclosed that new amide derivatives, and more particularly novel acylanilides, possess antiandrogenic properties.

In U.S. Pat. Nos. 3,995,060, 4,161,540 and 4,139,638, it is disclosed that certain 4'-substituted and 3'-, 4'-disubstituted anilides have antiandrogenic properties.

EP Pat. No. 138 504, EP Pat. No. 166 509, EP Pat No. 124 369, EP Pat. No. 160 508, EP Pat. No. 163 416, U.S. Pat. Nos. 4,732,912, 4,760,061, 4,751,240, 4,659,516 and Wakeling A. E. and Bowler J., J. Endocr. 112, R7–R10, 1987, and J. Steroid Biochem. 30, 141–147, 1988 disclose that certain long chain substitutions onto an estrogenic nucleus may result in compositions exhibiting antiestrogenic activity.

Chang et al., Biochemistry 21, 4102–4109, 1982, disclose the use of testosterone 17β-hemisuccinyl-3,3'-diaminodipropylamine-Sepharose 4B in the purification of androgen receptor.

De Larminat et al., The Prostate 5: 123–140, 1984, disclose the use of dihydrotestosterone- and testosterone-7α-undecanoyl agarose in the purification of androgen receptor.

Gyorki et al., J. Steroid Biochem. 25, 355–358, 1986, and Macaulay and Warne, J. Steroid Biochem. 26, 535–538, 1987, disclose the use of 7α-carboxyethinyl testosterone linked to Sepharose 4B in the purification of androgen receptor.

Salman et al., J. Steroid Biochem. 26, 383–391, 1987, disclose the use of 17α-hexynyl nortestosterone Sepharose in the purification of androgen receptor.

Grunwell et al., Steroids 27, 759–771, 1976, and Solo et al., Steroids 40, 603–614, 1982, disclose the synthesis of a series of 7α-alkyltestosterone derivatives and describe their biological activities.

For a number of years, there has been search for compounds which can efficiently inhibit androgen and/or estrogen formation without causing adverse effects to healthy tissues. More particularly, the inhibition of 17β-hydroxysteroid dehydrogenase, which is involved in the biosynthesis of testosterone, androst-5-ene-3β,17β-diol and estradiol, has been studied by some workers. Some affinity-label inhibitors for human placental estradiol 17β-dehydrogenase have been described (C. C. Chin and J. C. Warren, J. Biol. Chem. 250, 7682–7686, 1975; Y. M. Bhatnagar et al., J. Biol. Chem. 253, 811–815, 1978; C. C. Chin et al., J. Biol. Chem. 255, 3660–3664, 1980; J. L. Thomas and R. C. Strickler, J. Biol. Chem. 258, 1587–1590, 1983).

B. Tobias et al., J. Biol. Chem. 257, 2783–2786, 1982 and R. J. Auchus and D. F. Covey, Biochemistry 25, 7295–7300, 1986 disclose, respectively, the use of 17β-propynyl-substituted progestins and propynyl-substituted 3-hydroxy-14,15-secoestra-1,3,5(10)-trien-17-one as inhibitors of the 17β-estradiol dehydrogenase.

Thomas J. L. et al., J. Biol. Chem. 258, 11500, 1983 have described that 16-methylene estradiol and 16-methylene estrone are inhibitors of 17β-HSD activity.

French patent publication number 2,528,434 relates to the pharmaceutical use of 11β- and 2-substituted 19-nor-steroids.

OBJECTS OF THE INVENTION

It is an object of the present invention to provide methods of inhibiting sex steroid activity. Such methods may be useful in the treatment of sex steroid-related diseases.

It is another object of the invention to provide a steroidal pure antiandrogen for therapeutic use.

It is another object of the invention to provide compositions capable of inhibiting sex steroid synthesis, especially androgen synthesis.

It is another object to provide an antiandrogen having good affinity for androgen receptors, but substantially lacking undesirable agonistic activity regarding these receptors and substantially lacking hormonal activity.

It is another object of the invention to provide a therapeutic anti-androgenic composition useful in the treatment of androgen-related diseases. These diseases include, but are not limited to, prostate cancer, acne vulgaris, hirsutism, precocious puberty, benign prostatic hyperplasia, seborrhea, androgenic alopecia and sexual deviants. Control of androgen activity may also be useful in male contraception.

It is another effect of the invention to provide inhibitors of sex steroid production useful in the treatment of both estrogen- and androgen-related diseases. Estrogen-related diseases include but are not limited to breast cancer, uterine cancer, ovarian cancer, endometriosis, uterine fibroma, precocious puberty and benign prostatic hyperplasia.

SUMMARY OF THE INVENTION

The present invention provides a method of inhibiting sex steroid activity in a warm-blooded animal, including humans, comprising administering to said animal a therapeutically effective amount of a compound having an androgenic nucleus substituted at a ring carbon with at least one side chain represented by the formula —$R^1$[—B—$R^2$—]$_x$L—G wherein:

x is an integer from 0 to 6, wherein at least one of L and G is a polar moiety distanced from said ring carbon by at least three intervening atoms, and wherein:

$R^1$ and $R^2$ are independently either absent or selected from the group consisting of straight- or branched-chain alkylene, straight- or branched-chain alkynylene, straight- or branched-chain alkenylene, phenylene, and fluoro-substituted analogs of the foregoing;

B is either absent or selected from the group consisting of —O—, —S—, —Se—, —SO—, —$SO_2$—, —$NR^3$—, —$SiR^3_2$—, —$CR^3OR^3$—, —$NR^3CO$—, —$NR^3CS$—, —$CONR^3$—, —$CSNR^3$—, —COO—, —COS—, —SCO—, —CSS—, —SCS—, —OCO— and phenylene ($R^3$ being hydrogen or lower alkyl);

L is either a moiety which together with G, forms a heterocyclic ring having at least one nitrogen atom or is selected from the group consisting of lower alkyl, —$CONR^4$—, —$CSNR^4$—, —$NR^5CO$—, —$NR^5CS$—, —$NR^5CONR^4$—

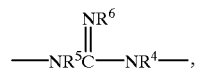

—$SO_2NR^4$—, —CSS—, —SCS—, —(NO)$R^4$—, —(PO)$R^4$—, —$NR^5COO$—, —$NR^5SO_2$—, —O—, —$NR^4$—, —S—, —SO—and —$SO_2$—($R^4$ and $R^5$ being independently selected from the group consisting of hydrogen and lower alkyl; and $R^6$ being selected from the group consisting of hydrogen, nitrile and nitro); and G is selected from the group consisting of hydrogen, lower alkyl, lower alkenyl, lower alkynyl, ($C_3$–$C_7$) cycloalkyl, bromo(lower)alkyl, chloro(lower)alkyl, fluoro(lower)alkyl, iodo(lower)alkyl, cyano(lower) alkyl, carboxy(lower)alkyl, (lower)alkoxycarbonyl (lower)alkyl, ($C_6$–$C_{10}$)aryl, ($C_7$–$C_{11}$)arylalkyl, di(lower)alkylamino(lower)alkyl, fluoro-substituted analogs of the foregoing, and a moiety which together with L forms a heterocyclic ring having at least one nitrogen atom.

The invention further provides a method of inhibiting sex steroid activity in a warm-blooded animal, including humans, comprising administering a therapeutically effective amount of at least one compound having, as part of its molecular structure, a substituted or unsubstituted nucleus of formula I:

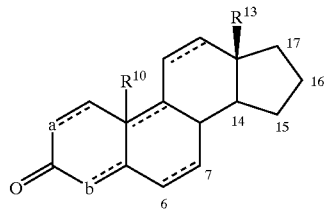

I wherein the dotted lines represent optional double bonds; a is a carbon or oxygen atom; b is carbon or nitrogen atom; $R^{10}$ and $R^{13}$ are independently hydrogen or lower alkyl; said compound further having, as a substituent to said nucleus in at least one position selected from the group consisting of 6α, 7α, 14α, 15α, 16α, 17α and 17β, a side chain of the formula —$R^1$[—B—$R^2$—]$_x$L—G, wherein:

x is an integer from 0 to 6, wherein L is separated from said androgenic nucleus by at least 3 atoms, and wherein:

$R^1$ and $R^2$ are independently either absent or selected from the group consisting of straight- or branched-chain alkylene, straight- or branched-chain alkynylene, straight- or branched-chain alkenylene, phenylene and fluoro-substituted analogs of the foregoing;

B is either absent or selected from the group consisting of —O—, —S—, —Se—, —SO—, —SO$_2$—, —NR$^3$—, —SiR$^3_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene ($R^3$ being hydrogen or lower alkyl);

L is either a moiety which together with G, forms a heterocyclic ring having at least one nitrogen atom or is selected from the group consisting of lower alkylene —CONR$^4$—, —CSNR$^4$—, —NR$^5$CO—, —NR$^5$CS—, —NR$^5$CONR$^4$—,

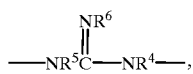

—SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO$_2$—, —SO— and —SO$_2$—(R$^4$ and R$^5$ being independently selected from the group consisting of hydrogen and lower alkyl; and R$^6$ being selected from the group consisting of hydrogen, nitrile and nitro); and G is selected from the group consisting of hydrogen, lower alkyl, lower alkenyl, lower alkynyl, (C$_3$–C$_7$) cycloalkyl, halo(lower)alkyl, carboxy(lower)alkyl, (lower)alkoxycarbonyl(lower)alkyl, (C$_6$–C$_{10}$)aryl, (C$_7$–C$_{11}$)arylalkyl, di(lower)alkylamino(lower)alkyl, fluoro-substituted analogs of the foregoing and a moiety which together with L forms a heterocyclic ring having at least one nitrogen atom.

As used herein, the term "sex steroid activity inhibitor" includes any compound which suppresses the activity of sex steroids by any mechanism including, for example, inhibition of sex steroid synthesis or antagonistic blocking of sex steroid receptors. "Androgen activity inhibitors" and "estrogen activity inhibitors" are sex steroid inhibitors capable of inhibiting the activity of androgens and estrogens, respectively. Inhibitors include, but are not limited to antiandrogens which block androgen receptors, thereby making them unavailable to androgen compounds which could otherwise activate those receptors. Androgen activity inhibitors also include compounds which inhibit the formation of compounds capable of activating androgen receptors such as inhibitors of production of natural androgens (e.g dihydrotestosterone) or inhibitors of production of precursors of natural androgens. One mechanism by which these androgen production inhibitors may operate is by blocking enzymes which catalyze production of natural androgens or their precursors (e.g. enzymes such as aromatase, 17β-hydroxysteroid dehydrogenase, 3β-hydroxysteroid dehydrogenase, 5α-reductase and the like).

As used herein, the term "androgenic nucleus" includes any compound which, in the absence of the side chain substituent specified herein, is capable of acting as an androgen as determined by a weight increase of at least 35 percent over a seven-day period of the prostates of castrated rats treated with the compound in question (15 milligrams twice daily per 100 grams of body weight) versus a control group of castrated rats. Treatment should start on the day of castration. The precise test, other than any parameters set forth in this paragraph, is that reported in Labrie et al., J. Steroid Biochem. 28, 379–384, 1987.

The present invention further provides for the treatment of sex steroid-related diseases by the methods of administering therapeutically effective amounts of sex-steroid activity inhibitors as disclosed herein (with or without pharmaceutical carriers or diluents). Sex steroid-related diseases include any disease whose onset, maintenance or progress is, at least in part, dependent upon biological activities induced by sex steroids such as androgens and estrogens. For example, androgen-dependent diseases include but are not limited to prostate cancer, acne vulgaris, hirsutism, precocious puberty, benign prostatic hyperplasia, seborrhea, androgen alopecia and sexual deviance. Control of androgenic activity may also be useful in male contraception.

The invention further provides a pharmaceutical composition comprising a pharmaceutically acceptable diluent or carrier and a therapeutically effective amount of a sex steroid activity inhibitor having an androgenic nucleus substituted at a ring carbon with at least one side chain represented by the formula —$R^1$[—B—$R^2$—]$_x$L—G wherein:

x is an integer from 0 to 6, wherein at least one of L and G is a polar moiety distanced from said ring carbon by at least three intervening atoms, and wherein:

$R^1$ and $R^2$ are independently either absent or selected from the group consisting of straight- or branched-chain alkylene, straight- or branched-chain alkynylene, straight- or branched-chain alkenylene, phenylene and fluoro-substituted analogs of the foregoing;

B is either absent or selected from the group consisting of —O—, —S—, —Se—, —SO—, —SO$_2$—, —NR$^3$—, —SiR$^3_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene ($R^3$ being hydrogen or lower alkyl);

L is either a moiety which together with G, forms a heterocyclic ring having at least one nitrogen atom or is selected from the group consisting of —CONR$^4$—, —CSNR$^4$—, —NR$^5$CO—, —NR$^5$CS—, —NR$^5$CONR$^4$—,

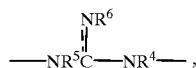

—SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO— and —SO$_2$— (R$^4$ and R$^5$ being independently selected from the group consisting of hydrogen and lower alkyl; and R$_6$ being selected from the group consisting of hydrogen, nitrile and nitro); and G is selected from the group consisting of hydrogen, lower alkyl, lower alkenyl, lower alkynyl, (C$_3$–C$_7$) cycloalkyl, halo(lower)alkyl, carboxy(lower)alkyl, (lower)alkoxycarbonyl(lower)alkyl, (C$_6$–C$_{10}$)aryl, (C$_7$–C$_{11}$)arylalkyl, di(lower)alkylamino(lower)alkyl, fluoro-substituted analogs of the foregoing and a moiety which together with L forms a heterocyclic ring having at least one nitrogen atom.

The invention further provides a sex steroid activity inhibiting compound having an androgenic nucleus substituted at a ring carbon with at least one side chain represented by the formula —R$^1$[—B—R$^2$—]$_x$L—G wherein:

x is an integer from 0 to 6, wherein at least one of L and G is a polar moiety distanced from said ring carbon by at least 8 atoms, and wherein:

R$^1$ and R$^2$ are independently either absent or selected from the group consisting of straight- or branched-chain alkylene, straight- or branched-chain alkynylene, straight- or branched-chain alkenylene, phenylene and fluoro-substituted analogs of the foregoing;

B is either absent or selected from the group consisting of —O—, —S—, —Se—, —SO—, —SO$_2$—, —NR$^3$—, —SiR$^3{}_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene (R$^3$ being hydrogen or lower alkyl);

L is either a moiety which together with G, forms a heterocyclic ring having at least one nitrogen atom or is selected from the group consisting of —CONR$^4$—, —CSNR$^4$—, —NR$^5$CO—, —NR$^5$CS—, —NR$^5$CONR$^4$—,

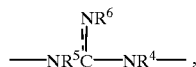

—SO$_2$NR$^4$—, —CSS—, —SCS—, —(NO)R$^4$—, —(PO)R$^4$—, —NR$^5$COO—, —NR$^5$SO$_2$—,—O—, —NR$^4$—, —S—, —SO— and —SO$_2$— (R$^4$ and R$^5$ being independently selected from the group consisting of hydrogen and lower alkyl; and R$^6$ being selected from the group consisting of hydrogen, nitrile and nitro); and G is selected from the group consisting of hydrogen, lower alkyl, lower alkenyl, lower alkynyl, (C$_3$–C$_7$) cycloalkyl, halo(lower)alkyl, carboxy(lower)alkyl, (lower)alkoxycarbonyl(lower)alkyl, (C$_6$–C$_{10}$)aryl, (C$_7$–C$_{11}$)arylalkyl, di(lower)alkylamino(lower)alkyl, fluoro-substituted analogs of the foregoing and a moiety which together with L forms a heterocyclic ring having at least one nitrogen atom.

The following conventions apply to structural formulae set forth herein. Unless specifically designated to the contrary, substituents may have either α or β stereochemistry or, where valence permits may represent one substituent in a position and another in β position. Presence of optional double bonds are independent of each other. All structures include salts thereof. Atoms of any androgenic nucleus for which no substituent is shown or described may optionally be substituted or unsubstituted so long as such substitution does not prevent the nucleus from functioning as an "androgenic nucleus" as defined herein. Those atoms having a defined substitutent may optionally be further substituted by other substituents where their valence permits such further substitution. As used herein, the term "lower", when describing a chemical moiety means a moiety having 8 or fewer atoms. For instance, a "lower alkyl" means a C$_1$ to C$_8$ alkyl. Any moiety of more than two atoms may be straight- or branched-chain unless otherwise specified.

DETAILED DESCRIPTION OF THE PREFERRED EMBODIMENTS

Figure 1:
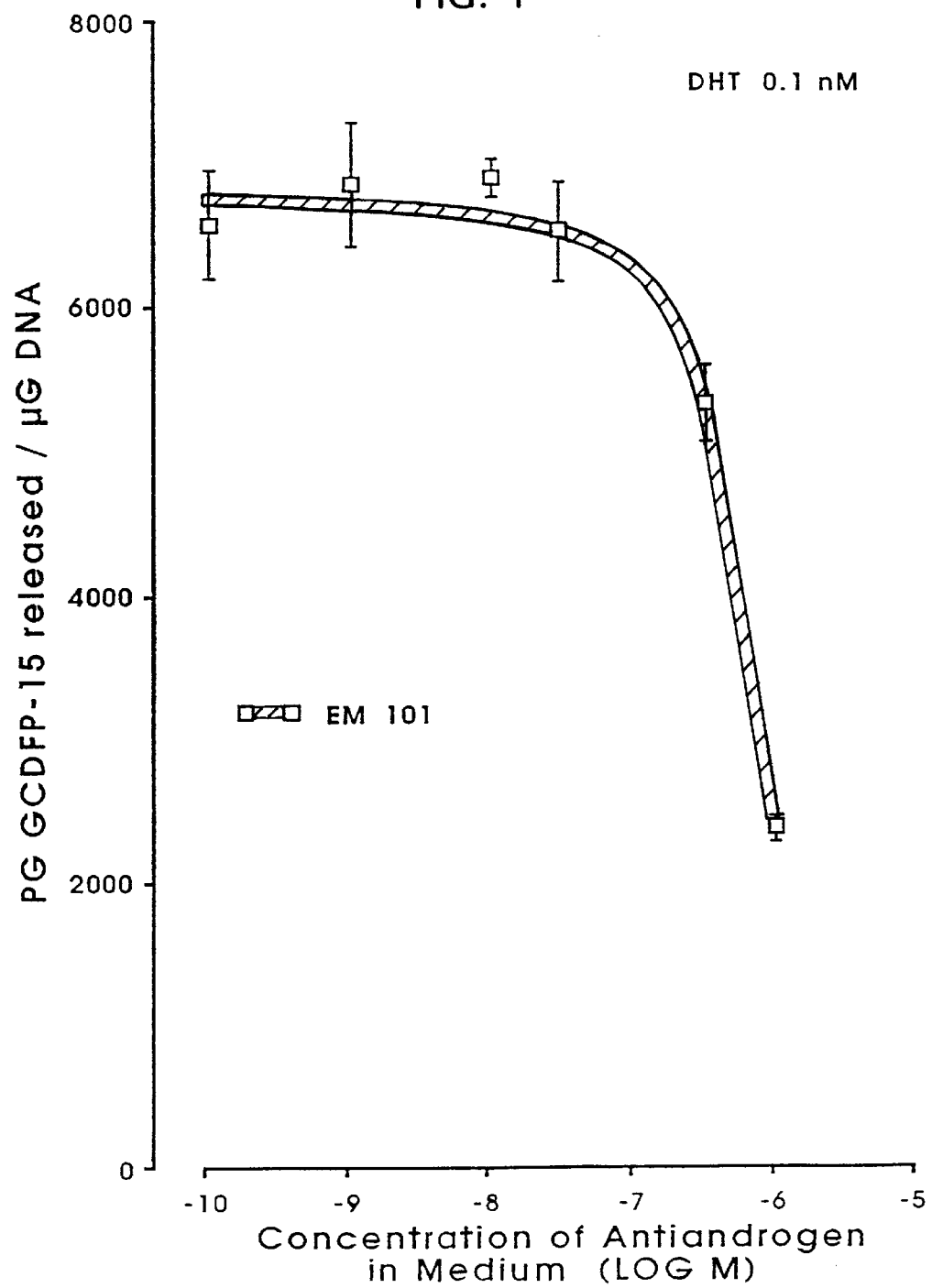
FIG. 1 is a graph illustrating the antiandrogenic activity of one preferred antiandrogen of the invention.

Preferred methods of treating of sex steroid-related diseases, especially androgen-related diseases, and preferred methods of blocking androgen receptors comprise administering to a patient in need of such treatment, a therapeutically effective amount of a sex steroid-activity inhibitors comprising an androgenic nucleus substituted with a side chain of the formula —R$^1$[—B—R$^2$—]$_x$L—G as defined above.

Preferred androgenic nuclei suitable for use in accordance with the invention are dihydrotestosterone and derivatives thereof, as well as testosterone and its derivatives. Other suitable androgenic nuclei include but are not limited to those which (as reported in the references set forth below) effect more than the threshold increase in prostate weight of castrated rats (Labrie C et al., J. Steroid Biochem. 28: 379–384, 1987; Labrie C et al., Endocrinology 123: 1412–1417, 1988; Plante et al., J. Steroid Biochem. 31: 64–74, 1988).

Some preferred androgenic nuclei are those of the general structure:

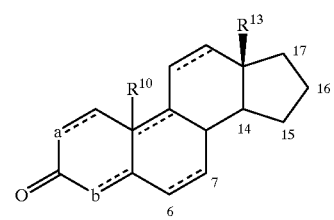

I wherein R$^{10}$ and R$^{13}$ are independently hydrogen or lower alkyl.

In some preferred embodiments, a and b of structure I are carbon atoms or a is carbon and b is nitrogen. Preferably, the nucleus is substituted in the 17β position with hydroxyl or $(C_1-C_{20})$alkanoyloxy.

Other preferred androgenic nuclei have the structure:

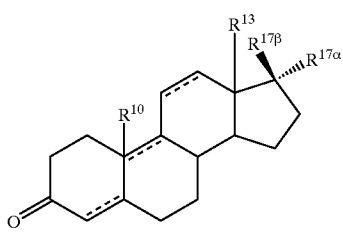

II wherein $R^{10}$ and $R^{13}$ are independently hydrogen or lower alkyl;

$R^{17(\alpha)}$ is selected from the group consisting of hydrogen, hydroxyl, lower alkanoyloxy, lower alkyl, lower alkenyl, lower alkynyl, halo(lower)alkyl, halo(lower)alkenyl, halo(lower)alkynyl and fluoro-substituted aromatic ring.

$R^{17(\beta)}$ is selected from the group consisting of hydroxyl, $(C_1-C_{20})$ alkanoyloxy, $C_3-C_7$)alkenoyloxy, $C_3-C_7$) alkynoyloxy, aroyloxy, alkenoyloxy, cycloalkenyloxy, 1-alkyloxy-alkyloxy, 1-alkyloxycycloalkyloxy, alkylsilyloxy, carboxyl, alkanoyl, or $R^{17(\alpha)}$ and $R^{17(\beta)}$ together are represented by the formula:

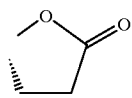

III

Other preferred androgenic nuclei have the structure:

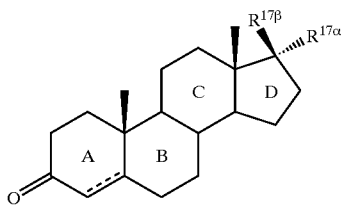

IV wherein: $R^{17(\alpha)}$ is selected from the group consisting of hydrogen, hydroxyl, lower alkanoyloxy, lower alkyl, lower alkenyl, lower alkynyl, halo(lower)alkyl, halo(lower)alkenyl, halo(lower)alkynyl and fluoro-substituted aromatic ring.

$R^{17(\beta)}$ is selected from the group consisting of hydroxyl, $(C_1-C_{20})$alkanoyloxy, $(C_3-C_7)$alkenoyloxy, $(C_3-C_7)$ alkynoyloxy, aroyloxy, alkenoyloxy, cycloalkenyloxy, 1-alkyloxy-alkyloxy, 1-alkyloxycycloalkyloxy, alkylsilyloxy, carboxyl, alkanoyl, or $R^{17(\alpha)}$ and $R^{17(\beta)}$ together are represented by the formula:

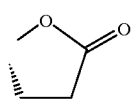

III

The AB-ring junction, in preferred embodiments, has trans configuration.

When sex steroid activity inhibitors are administered in accordance with the invention, they are preferably administered as a dosage from about 1 mg to about 2000 mg of active expedient (i.e. sex steroid activity inhibitor), per day per 50 kg of body weight, most preferably from about 10 mg to about 100 mg per day per kg of body weight.

The sex steroid activity inhibitors are preferably prepared as pharmaceutical compositions together with pharmaceutically acceptable carriers and diluents. When prepared for parenteral injection, an inhibitor of sex steroid activity is preferably added at a concentration between about 1 mg/ml and about 100 mg/ml (preferably about 2 mg/ml to about 10 mg/ml) into a carrier preferably selected from the group consisting of saline, water, aqueous ethanol, aqueous dimethylsulfoxide and oil.

When a pharmaceutical composition of the invention is prepared for oral ingestion, the composition preferably included at least one inhibitor of sex steroid activity wherein the total concentration of all such inhibitors in said pharmaceutical composition is from about 1% to about 95% of the composition (by weight), and preferably from about 5% to about 20%. The composition preferably further includes a pharmaceutically acceptable diluent, for example, starch or lactose with or without tartrazine. Slow release pharmaceutical products comprising the novel inhibitors of sex steroid activity may be incorporated into slow release pharmaceutical products which, other than addition of the novel inhibitors, may be prepared by known methods and administered orally as well as parenterally.

It is preferred that at least one side chain —$R^1$[—B—$R^2$—]$_x$L—G be substituted onto an androgenic nucleus at either the 6α, 7α, 14α, 15α, 16α, 17α or 17β position (for locating these positions. See structural formula I above). Especially preferred are the 15α, 17α and particularly 7α positions. In the above side-chain structure, L is preferably separated from the androgenic nucleus by at least 3 intervening and preferably 6 atoms. A polar moiety (G, L or both) is preferably separated from the androgenic nucleus by at least 8 intervening atoms.

In certain embodiments of the invention, $R^{17(\beta)}$ substituents are hydroxyl or one of its ester derivatives, such as acetate, oenanthate, cypionate and trans-4-n-butyl-cyclohexanecarboxylate. It is also preferred that the side chain $R^1$[—B—$R^2$—]$_x$ L—G have between about 7 and 30 carbon atoms. In certain embodiments, therapeutic compositions may comprise one or more sex steroid activity inhibitors represented by the formula V below:

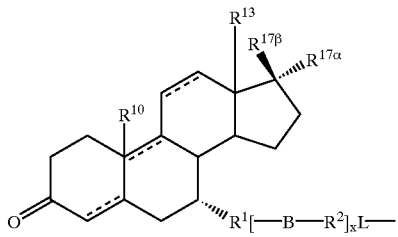

V wherein $R^{10}$ is preferably absent, hydrogen or methyl in β configuration, wherein $R_{13}$ is hydrogen or lower alkyl. Other preferred sex steroid activity inhibitors include those of formula VI below (or its 17β-ester derivatives) which illustrates one preferred side chain at the 7α position.

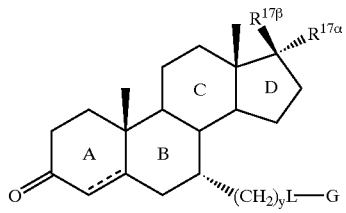

VI wherein y is preferably an integer from 4 to 20;
  wherein L is preferably —CONR$^4$—, —CSNR$^4$—, —NR$^5$CO—, —NR$^5$CS— or —CH$_2$—(R$^4$ and R$^5$ being hydrogen or methyl) and G is preferably n-propyl, n-butyl, n-pentyl or halo(lower)alkyl;
  wherein the AB-ring junction is preferably trans; and the dotted line represents an optional double bond;
  wherein R$^{17(\beta)}$ is preferably hydroxyl or alkanoyloxy; wherein R$^{17(\alpha)}$ is hydrogen or lower alkyl or R$^{17(\alpha)}$ or R$^{17(\beta)}$ together are represented by the formula:

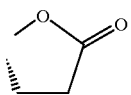

III

Structures V and VI represent preferred antiandrogens for use in the treatment of prostate cancer and other androgen-related diseases where the combination of androgen receptor blocking and androgen synthesis inhibition is desirable.

The inhibitors of sex steroid activity may be used in combination with surgical or chemical castration and/or other inhibitors of sex steroid activity, especially those which act upon other enzymes involved in synthesis of sex steroids or their precursors.

Another preferred androgen-activity inhibitor is one of the general formula V below (or its 17β-ester derivatives) which illustrates that positions 10 and 13 (for locating these positions, see structural formula V above) are preferably methylated in the β configuration, and that a 17β hydroxyl is also preferred:

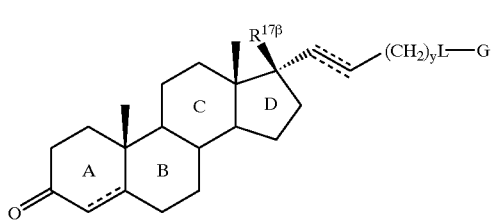

VII wherein the AB-ring junction is trans, the dotted lines in the A-ring represents optional pi bonds; y is an integer from 4 to 20, L is selected from the group consisting of —CONR$^4$—, —CSNR$^4$—, —NR$^5$CR—, —NR$^5$CS— or —CH$_2$—(R$^3$ and R$^4$ being hydrogen or methyl) and G either is n-propyl, n-butyl, n-pentyl or haloalkyl.

EXAMPLES OF SYNTHESIS OF PREFERRED INHIBITORS OF SEX STEROID ACTIVITY

Instrumentation

The IR spectra were taken on a Perkin-Elmer 1310 spectrophotometer. Proton NMR spectra were recorded on a Varian EM-360A (60 MHz, when specified) or a Varian XL-200 (MHz) instrument. The following abbreviations have been used: s, singlet; d, doublet; dd, doublet of doublet; t, triplet; q, quadruplet; and m, multiplet. Chemical shifts are reported in δ values in ppm relative to tetramethysilane (TMS) as internal standard. Mass spectra (MS) were obtained on a V.G. Micromass 16F machine. Thin-layer chromatography (TLC) was performed on 0.25 mm Kieselgel 6OF254 plates (E. Merck, Darmstadt, FRG). For flash chromatography, Merck-Kieselgel 60(230–400 mesh A.S.T.M.) was used. All solvents used in chromatography has been distilled. Unless otherwise note, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Anhydrous solvents were prepared in the following way.

| SOLVENT | DISTILLED OVER |
|---|---|
| AMINE, DIMETHYLFORMAMIDE | CaH$_2$ |
| HEXANE, DICHLOROMETHANE | P$_2$O$_5$ |
| ACETONE | K$_2$CO$_3$ |
| BENZENE | LiAlH$_4$ |
| TOLUENE | Na |
| ETHER, TETRAHYDROFURAN | LiAlH$_4$, Na Benzophenone |

EXAMPLE 1

Synthesis of N-butyl, N-methyl-11-(17'β-hydroxy-4'-androsten-3'-on-7'α-yl) undecanamide (5, x=10) (Scheme 1) 17β-acetoxy-7α-(11'-hydroxy undecanyl)-4-androsten-3-one (2)

Under argon atmosphere, in a flame dried apparatus with magnetic stirrer, a solution of 11-bromo undecanol tetrahydropyranyl ether (25 g, 74 mmol) in anhydrous THF (150 ml) was added dropwise to iodine-activated magnesium (1.9 g). The mixture was kept at room temperature overnight and then was cooled to −30° C. and anhydrous cuprous chloride (0.3 g) was added quickly. After 45 min of stirring at this temperature, commercial 4,6-androstadien-17β-ol-3-one acetate (1) (10 g, 30.5 mmol) in anhydrous THF (100 ml) was added dropwise during 4 h. After 35 min, acetic acid (6 ml) and water (100 ml) was added. The mixture was allowed to reach room temperature and was stirred overnight. Afterwards, the organic compound was extracted with ether (3X). The organic layers were washed with water, dried on magnesium sulfate and evaporated. The residue was dissolved in acetic acid (35 ml) and water (100 ml) and kept 48 h at room temperature. And then, the organic compounds were extracted with ether (3X). The organic layers were washed with saturated sodium bicarbonate solution and water, dried on magnesium sulfate and evaporated. The product was purified by Silica gel dry column chromatography (Kieselgel, 6OF254, Merk, 0.063–0.200 mm, 150 g). Elution with a mixture of methylene chloride and ethyl acetate (20:1 v/v) gave 17β-acetoxy-7α-(11'-hydroxy-undecanyl)-4-androsten-3-one (2a, 1.46 g, 2.8 mmol, 9.2%) as a colorless oil; IR ν$_{max}$ neat 3450, 1740, 1685, 1620 and 1245 cm$^{-1}$; NMR 0.84 (s, 3H, 18'-CH$_3$), 1.21 (s, 3H, 19'-CH$_3$), 2.05 (s,3H, OCOCH$_3$), 3.61 (t, 2H, J=6.59 Hz, H-C.1'), 4.61 (t, 1H, J=7.69 Hz, H-C.17) and 5.73 (s, 1H, H-C.4) and 17β-acetoxy-7β-(11'-hydroxy undecanyl)-4-androsten-3-one (2b, 0.9 g, 1.7 mmol, 5.6%) as a colorless oil.

11-(17'β-acetoxy-4'-androsten-3'-on-7'α-yl)undecanoic acid (3)

To 17β-acetoxy-7α-(11'-hydroxy undecanyl)-4-androsten-3-one (2a, 800 mg, 1.6 mmol) dissolved in acetone (50 ml) and cooled to 0° C. was added under stirring during 5 min, a solution of Jones' reagent (8N chromic acid solution) (0.283 ml). After 15 min, isopropanol (0.5 ml) was added followed by water and the mixture was extracted with ethyl acetate (3X). The organic layers were washed with brine, dried on magnesium sulfate and evaporated to dryness under reduced pressure. The crude 11-(17'β-acetoxy-4'-androsten-3'-on-7'α-yl) undecanoic acid (3) (740 mg) was used in the next step without purification.

N-butyl, N-methyl-11-(17'β-acetoxy-4'-androsten-3'-on-7'α-yl) undecanamide (4)

To a solution of the above undecanoic acid derivative 3 (390 mg, 0.78 mmol) in anhydrous methylene chloride (8 ml) cooled at −10° C. was added, under stirring, triisobutylamine (240 μl) and isobutylchloroformate (140 μl). After 30 min, N-methylbutylamine (1.8 ml) was added and the mixture was stirred at room temperature for 1 h. Methylene chloride was added. The organic solution was washed with 1N hydrochloric acid, water, saturated sodium bicarbonate solution and finally with water, dried on magnesium sulfate and evaporated to dryness. The residue was chromatographed on silica gel (Kieselgel, 60F254, Merck, 0.063–0.200 mm, 20 g). Elution with a mixture of diethyl ether and methylene chloride (1:20, v/v) gave N-butyl, N-methyl-11-(17'β-acetoxy-4'-androsten-3'-on-7'α-yl) undecanamide 4 (230 mg, 0.39 mmol, 46% for the alcohol (2a )) as a colorless oil; IR $\mu_{max}$ neat 1740, 1680, 1640 and 1240 cm$^{-1}$; NMR 0.84 (s, 3H, 18'-CH$_3$), 0.95 (t, 3H, J=6.93 Hz, N—(CH$_2$)$_3$CH$_3$), 1.21 (s, 3H, 19'-CH$_3$), 2.04 (s, 3H, OCOCH$_3$), 2.91 and 2.97 (2s, 3H, N—CH$_3$), 3.26 and 3.36 (2t, 2H, J=7.86 Hz, N—CH$_2$C$_3$H$_7$), 4.61 (t, 1H, J=8.42 Hz, H—C.17') and 5.72 (s, 1H, H—C.4').

N-butyl, N-methyl-11-(17'β-hydroxy-4'-androsten-3'-on-7'α-yl) undecanamide (5) (EM 101)

The above acetoxy amide 4 (170 mg, 0.29 mmol) was dissolved in methanol (20 ml) and 6% potassium carbonate (2 ml) and heated at 65° C. for 200 min. After cooling, acetic acid (1 ml) and water (150 ml) were added and the mixture was extracted with ethyl acetate (3x). The organic layers were washed with water, dried on magnesium sulfate and evaporated to dryness. The residue was purified by Silica gel dry column chromatography (Kieselgel, 60F254, Merk, 0.063–0.200 mm, 20 g). Elution with a mixture of diethyl ether and methylene chloride (1:9, v/v) gave N-butyl-N-methyl-11-(17'β-hydroxy-4'-androsten-3'-on-7'α-yl) undecanamide (EM 101, 94 mg, 0.17 mmol, 58%) as a colorless oil; IR $v_{max}$ (neat) 3400, 1670 and 1640 cm$^{-1}$; NMR 0.80 (s, 3H, 18'—CH$_3$), 0.95 (t,3H, J=6.75 Hz, N—(CH$_2$)$_3$CH$_3$), 1.21 (s, 3H, 19'—CH$_3$), 2.91 and 2.97 (2s, 3H, N—CH$_3$), 3.25 and 3.35 (2t 2H, J=7.3Hz, N-CH$_2$C$_3$H$_7$), 3.67 (t, 1H, J=8.18, H-C.17') and 5.72 (s, 1H, H-C.4').

N-butyl, N-methyl-11-(17'β-benzoyloxy-4'-androsten-3'-on-7'α-yl) undecanamide (6)

The 17β-alcohol 5 obtained previously (55 mg, 0.10 mmol) are dissolved in pyridine (1 ml) and benzoyl chloride (0.1 ml) and kept under stirring overnight at room temperature. Then, the mixture was poured in ice-water and extracted with ether (3x). The organic layers were washed with 1N HCl water, saturated sodium bicarbonate solution and finally with water, dried on magnesium sulfate and evaporated to dryness. The residue was purified by Silica gel dry column chromatography (Kieselgel, 60F254, Merck, 0.063–0.200 mm, 10 g). Elution with a mixture of diethyl ether and methylene chloride (1:20 v/v) gave the N-butyl, N-methyl-11-(17β-benzoyloxy-4'-androsten-3'-on-7'α-yl) undecanamide (6, R=C$_6$H$_5$CO) (45 mg, 0.07 mmol, 70%) as a colorless oil.

SCHEME 1

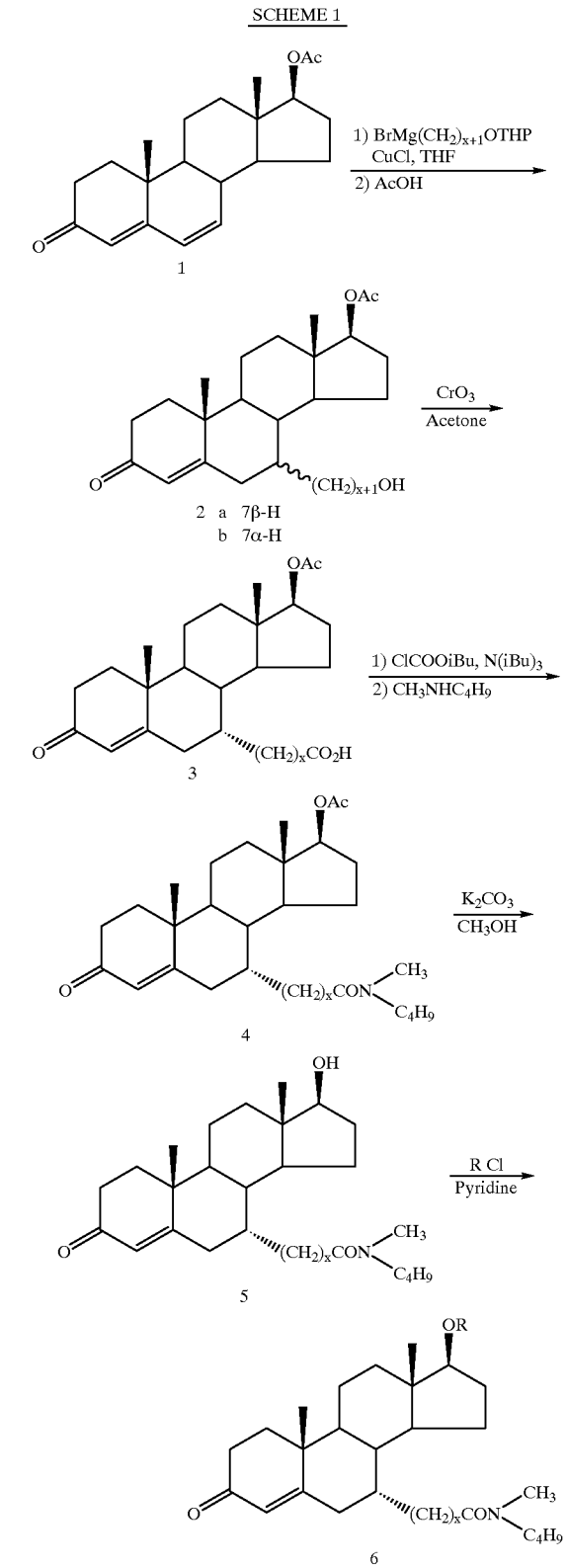

TABLE 1

Ester of N,N'-dialkyl-11-
(17'β-hydroxy-4'-androsten-3'-on-7'α-yl) alkylamide

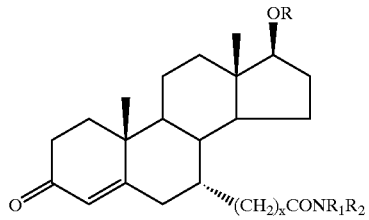

| x | R | $R_1$ | $R_2$ |
|---|---|---|---|
| 14 | H | methyl | n-butyl |
| 14 | $CH_3CO$ | methyl | n-butyl |
| 12 | H | methyl | n-butyl |
| 12 | $CH_3CO$ | methyl | n-butyl |
| 10 | H | H | n-butyl |
| 10 | H | methyl | 1H,1H-heptafluorobutyl |
| 10 | H | methyl | n-pentyl |
| 10 | $C_6H_3CO$ | methyl | n-butyl |
| 10 | $C_2H_5CO$ | methyl | n-butyl |
| 10 | trans-4-n-butyl-cyclo $C_6H_{10}CO$ | methyl | n-butyl |
| 10 | cyclo $C_5H_9$—$CH_2CO$ | methyl | n-butyl |
| 8 | H | H | n-butyl |
| 8 | H | methyl | n-butyl |
| 8 | $CH_3CO$ | methyl | n-butyl |
| 6 | H | methyl | n-butyl |
| 6 | $CH_3CO$ | methyl | n-butyl |

By analogous methods to those described above and using the same or other tetrahydropyranyloxy bromoalkane, the same or other dialkylamine and the same or other acid chloride, the following compounds, described in Table 1, are synthesized.

Efficacy of an Antiandrogen Synthesized in Accordance with Example 1

Compound 5 ("EM 101") shown in Scheme 1 above is itself an androgen activity inhibitor as well as intermediate in the synthesis of compounds 6. EM 101 has been tested both for efficacy in acting as an antiandrogen by blocking androgen receptors without substantially activating those receptors, and for efficacy in inhibiting 17β-hydroxysteroid dehydrogenase, an enzyme which catalyzes reactions involved in the synthesis of both androgens and estrogens (hereinafter referred to as "17β-HSD").

The efficacy of EM 101 as an antiandrogen is shown in FIG. 1. Human mammary cancer cells ZR-75-1 contain androgen receptors. They secrete the gross cystic disease fluid protein (GCDFP-15) and this secretion is stimulated by androgens. ZR-75-1 cells were seeded at 9000 cells/plate in multiwell dishes in medium containing 2% dextran-coated charcoal-treated fetal calf serum. Three days after plating, the medium was changed and the compounds to be tested were added to triplicate dishes. Increasing concentrations of EM 101 were added in medium containing 0.1 nM dihydrotestosterone (DHT). This concentration of DHT in the absence of antiandrogen causes about a 3-fold increase in GCDFP-15 secretion. Medium was changed every 2–3 days and collected after 12 days of incubation (48 hours after the last change). GCDFP-15 was measured by radioimmunoassay. Cells were collected and the total DNA content was measured by fluorometry. GCDFP-15 was expressed as pg GCDFP-15/μg DNA. As shown in FIG. 1, increasing concentrations of EM 101 significantly inhibited the DHT-induced GCDFP-15 secretion, thus indicating an antiandrogenic action of EM 101 in this in vitro system.

Figure 2:
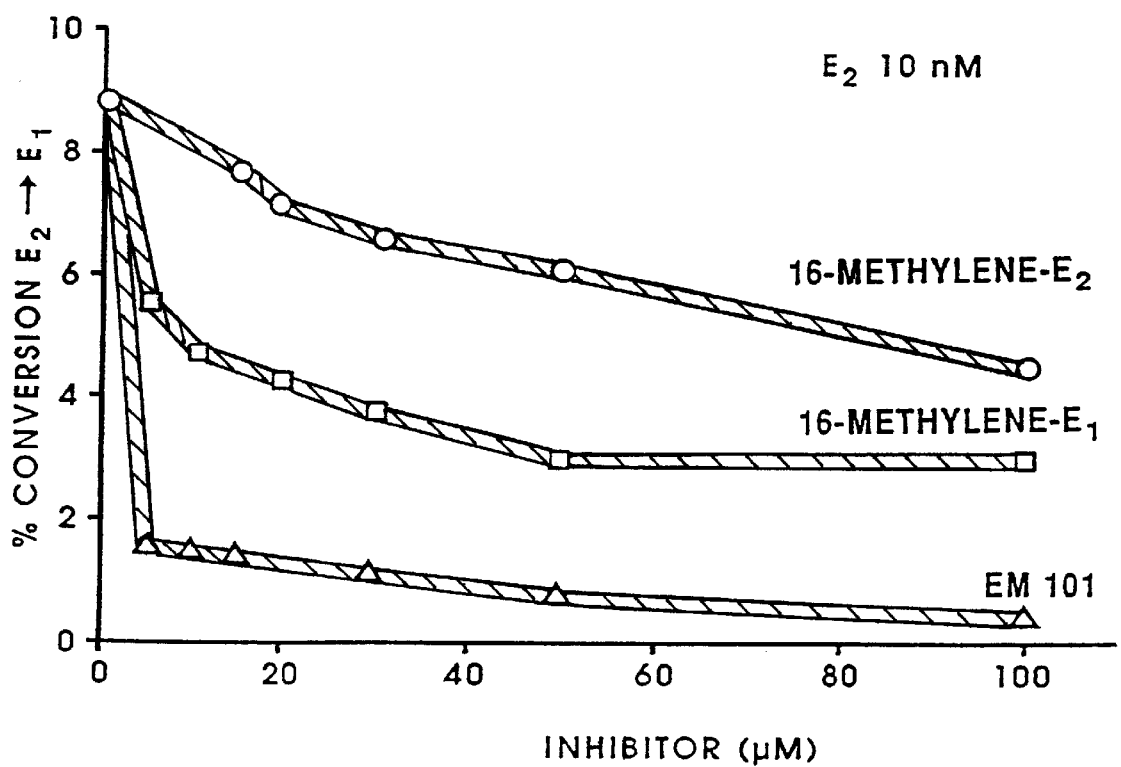
FIG. 2 is a graph illustrating that the antiandrogen which is the subject of FIG. 1 is also a good inhibitor of sex steroid synthesis as compared to other known synthesis inhibitors.

To compare the effect of EM 101 to known inhibitors of 17β-HSD (16-methylene-$E_1$ and 16-methylene-$E_2$), rat ovaries were homogenized in $KH_2PO_4$ (20 mM), EDTA (1 mM) and glycerol (20%) at pH 7.5, and 1000 g pellets were discarded. A reaction vessel was prepared containing 100 μl of homogenate, $NAD^+$ (1 mM), $NADP^+$ (1 mM), [$^3H$] estradiol (10 mM), an inhibitor (either EM 101, 16-methylene $E_1$ or 16-methylene-$E_2$) at different concentrations indicated on the X-axis of FIG. 2, and the volume was completed to 1 ml with phosphate buffer [$KH_2PO_4$ (12.5 mM), EDTA (1 mM) pH 7.5]. The reaction was allowed to proceed at 37° C. for 20 min. After methylene chloride extraction (2X), the organic phase was dried on magnesium sulfate and evaporated under a stream of nitrogen. The residue was dissolved in methanol and separated by thin layer chromatography on aluminium-coated silica-gel plates (benzene acetone 4:1). Spots were cut, dissolved in ethanol and counted using Formula 963 as scintillation fluid. The conversion of estradiol ($E_2$) into estrone ($E_1$) (a 17β-HSD-catalyzed reactions) was measured. As shown in FIG. 2, increasing concentrations of EM 101 inhibited this conversion more rapidly and completely than did the two known 17β-HSD inhibitors 16-methylene-$E_1$ and 16-methylene-$E_2$.

EXAMPLE 2

Synthesis 17β-hydroxy-17α-(ω-iodoalkynyl)-4-androsten-3-one (9) (Scheme 2)

(±)3,3-ethylenedioxy-17β-tetrahydropyranyloxy-17α-ethynyl-5-androstene (8)

A mixture of ethisterone (7) (9.5 g, 30.4 mmol), ethylene glycol (3.34 g, 3 ml, 53.8 mmol) and p-toluenesulfonic acid (50 mg, 0.29 mmol) dissolved in 500 ml of dry benzene was refluxed (Dean-Stark) for 24 h under nitrogen. Then, a mixture of ether and dichloromethane (1:1, 1 L) was added and the resulting solution washed successively with sodium carbonate (2×100 ml, 5% aqueous) and with water (4×200 ml). The organic phase was dried, filtered and concentrated to dryness. The crude 3,3-ethylenedioxy-17α-ethynyl-5-androsten-17β-ol (9.73 g, 90% of crude dioxolane) was used without any further purification in the next step.

A mixture of crude dioxolane (9.73 g, 27.3 mmol) in dry dichloromethane (500 ml), 2,3-dihydropyran (6.9 g, 7.5 ml, 82.2 mmol), and catalytic pyridinium p-toluenesulfonate (100 mg, 0.4 mmol) was stirred at room temperature for 36 h. Then, ether (500 ml) was added and the resulting solution was washed successively with sodium carbonate (2×100 ml, 5% aqueous) and with water (4×200 ml). The organic phase was dried, filtered and evaporated to give 12.74 g of crude material. The residue was purified by flash chromatography (hexane: acetone, 95:5) to give compound 7 (7.7 g, 58%); IR(KBr)ν max: 3300 and 3230 ($\equiv$C—H), 2090 (C$\equiv$C) and 1150–980 (C—O) cm$^{-1}$; $^1$H-NMR (60 MHz) 5.35–4.80 (2H,m,—C=CH—, —OC$\underline{H}$OC$\underline{H}_2$—), 3.88 (4H,s,—OC$\underline{H}_2$C$\underline{H}_2$O—), 2.50 (1H,s,—C$\equiv$C—H), 1.00 (3H,s,19-C$\underline{H}_3$), 0.88 (3H,s,18-C$\underline{H}_3$); MS m/e (70 eV): 440 ($M^+$). Further elution gave the corresponding enone (2.94 g, 24%).

(±)3,3-Ethylenedioxy-17β-tetrahydropyranyloxy-17α-(5'-iodopentynyl)-5-androstene (8, n=3)

To a solution of butyllithium (2.84 ml of a 1.6 M solution in hexane, 4.5 mmol) in dry tetrahydrofuran (THF, 30 ml) was added dropwise a solution of diprotected ethisterone 7 (500 mg, 1.13 mmol) in dry THF (10 ml) at −40° C. The reaction mixture was then allowed to warm up to −10° C. and stirred for 1 h. At this temperature, a solution of 1,3-di-iodopropane (1.61 g, 627 μl, 5.4 mmol) in dry THF (5 ml) was added in one portion. The cooling bath was removed and the reaction mixture was stirred at room temperature for 15 h. Then, the solution was diluted with 100 ml of ether and was washed with water (6×30 ml), dried, filtered and concentrated to an oil. The residue was purified by flash chromatography (hexane: acetone, 95:5) followed by preparative thin-layer chromatography (TLC) (benzene: acetone, 95:5, Rf 0.68) to give compound 8 (n=3) (302 mg, 43%); 1H-NMR 5.35–4.80 (2H,m,—C═CH—, —OC$\underline{H}$OC$\underline{H}_2$—), 3.88 (4H,s,—OC$\underline{H}_2$C$\underline{H}_2$O—), 3.23 (2H,t,j=6.0 Hz,—C$\underline{H}_2$I), 1.02 (3H,s,19-C$\underline{H}_3$), 0.89 (3H,s,18-C$\underline{H}_3$).

17β-Hydroxy-17α-(5'-iodopentynyl)-4-androsten3-one (9, n=3)

To a solution of the oily tetrahydropyranyl ethers 8 (n=3) (38 mg, 6.25×10–2 mmol) in ethanol (5 ml) was added oxalic acid (2 ml, 2% aqueous). The reaction mixture was heated at reflux for 2.5 h. Then, most of the ethanol was evaporated and the residue, transferred into a separatory funnel with ether (40 ml) and water (20 ml) was washed thoroughly with water. The ethereal phase was dried, filtered and concentrated to an oil. The residue was purified by preparative TLC (benzene: acetone, 95:5, Rf 0.26) to give 17β-hydroxy-17α-(5'-iodopentynyl)-4-androsten-3-one (9, n=3) as colorless oil; IR (neat) ν max: 3600–3150 (OH), 2230 (C≡C), 1660 (C═O) and 1610 (C═C) cm$^{-1}$; $^1$H-NMR 5.74 (1H,s, —C$\underline{H}$═C—), 5.29 (2H,t,J=6.6 Hz, —C$\underline{H}_2$I), 1.20 (3H,s,19-C$\underline{H}_3$), 0.88 (3H,s,18-C$\underline{H}_3$); MS m/e (70eV): 480 (M$^+$).

(±)3,3-Ethylenedioxy-17β-tetrahydropyranyloxy-17α-(8'-iodooctynyl)-5-androstene (8, n=6)

The preparation of this derivative was done as described for alkyl iodide 8 (n=3) (vide supra) with the following quantities: acetylene 7 (570 mg, 1.29 mmol), butyllithium (2.07 ml of a 2.5 M solution in hexane, 5.17 mmol), 1,6-diiodohexane (2.1 g, 6.2 mmol), tetrahydrofuran (50 ml). The crude material was purified by flash chromatography (hexane: acetone, 95:5) to give compound 8 (n=6) (260 mg, 30.5%) as colorless oil; IR (neat) ν max 2220 (C≡C) and 1150–980 (C—O) cm$^{-1}$; $^1$H-NMR 5.35 (1H,m,—C═CH—), 5.15 and 4.94 (1H, 2m,—OC$\underline{H}$OCH$_2$—), 3.95 (4H, m,—OC$\underline{H}_2$C$\underline{H}_2$—), 3.50 (1H,m,—OCHOC$\underline{H}\underline{H}$—), 3.20 (2H,t,J=6,96 Hz,—C$\underline{H}_2$I), 2.58 (1H,d of m, J=13.5 Hz,—OCHOC$\underline{H}\underline{H}$—),1.04 and 1.03 (3H, 2s,19-C$\underline{H}_3$), 0.88 (3H,s,18-C$\underline{H}_3$); MS m/e (70eV): 650 (M$^+$).

17β-Hydroxy-17α-(8'-iodooctynyl)-4-androsten-3-one (9, n=6)

The hydrolysis of compound 8 (n=6) was done as described for tetrahydropyranyl ethers 8 (n=3) (vide supra) with the following quantities: tetrahydropyranyl ethers 8 (n=6) (24 mg, 3.69×10$^{-2}$ mmol), oxalic acid (1.5 ml, 2% aqueous), ethanol (5 ml). The crude material was purified by preparative TLC (hexane: acetone, 9:1, Rf 0.17) to give 17β-hydroxy-17α-(8'-iodooctynyl)-4-androsten-3-one (9, n=6) (18 mg, 93%) as colorless oil; IR (neat) ν max 3600–3150 (OH), 2225 (C≡C), 1660 (C═O) and 1610 (C═C) cm$^{-1}$; $^1$H-NMR: 5.74 (1H,s,—C$\underline{H}$═C—), 3.17 (2H, t,J=6.96 Hz, —C$\underline{H}_2$I), 1.20 (3H,s,19-C$\underline{H}_3$), 0.88 (3H,s,18-C$\underline{H}_3$); MS m/e (70eV): 522 (M$^+$).

(±)3,3-Ethylenedioxy-17β-tetrahydropyranyloxy-17α-(12'-iodododecynyl)-5-androstene (8, n=10)

The preparation of this derivative was realized as described for alkyl iodide 8 (n=3) (vide supra) with the following quantities: acetylene 7 (500 mg, 1.13 mmol), butyllithium (2.84 ml of a 1.6 M solution in hexane, 4.54 mmol), 1,10-diiodododecane (2.15 g, 5.45 mmol), tetrahydrofuran (45 ml). The crude material was purified by flash chromatography (hexane: acetone, 96:4) to give compound 8 (n=10)

SCHEME 2

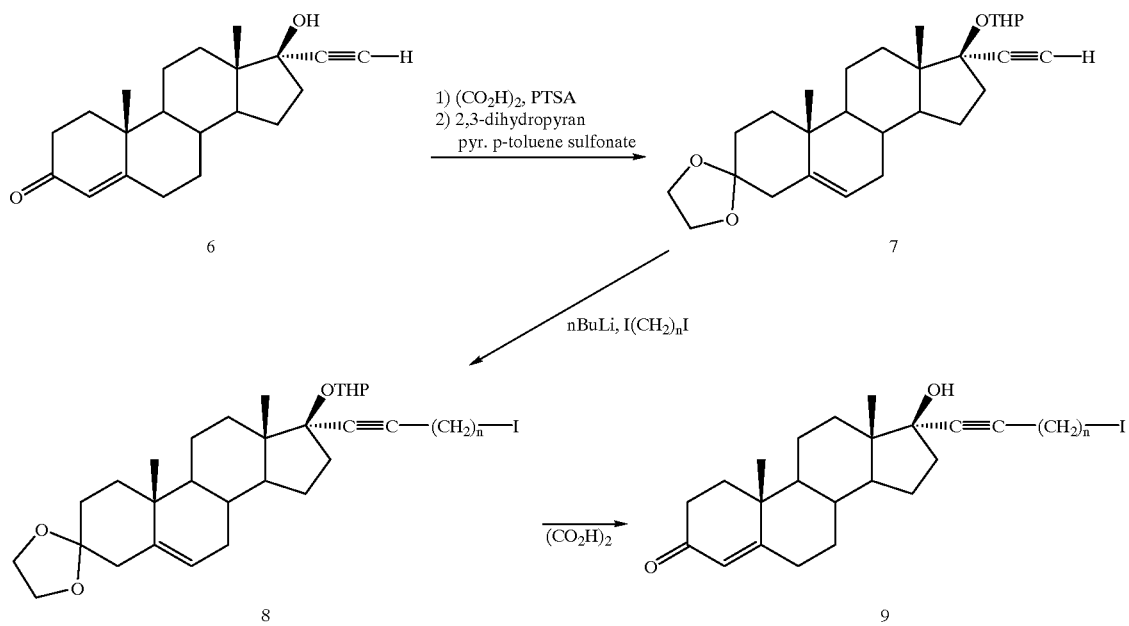

(208 mg, 26%) as colorless oil; IR (neat) ν max 2240 (C≡C) and 1150–980 (C—O) cm$^{-1}$; $^1$H-NMR: 5.36 (1H, m,—C═C$\underline{H}$—), 5.18 and 4.97 (1H,2m,—OC$\underline{H}$OCH$_2$—), 3.95 (4H,m,—OC$\underline{H}_2$C$\underline{H}_2$O—), 3.50 (1H,m,—OC$\underline{H}$OC $\underline{H}\underline{H}$—), 3.19 (2H,t,J=6,96 Hz,—C$\underline{H}_2$I), 2.58 (1H,m,—OCHOC$\underline{H}\underline{H}$—),1.04 and 1.03 (3H,2s,19-C$\underline{H}_3$), 0.88 (3H,s, 18-C$\underline{H}_3$); MS m/e (70eV): 706 (M$^+$).

17β-Hydroxy-17α-(12'-iodododecynyl)-4-androsten-3-one ("EM 150", 9, n=10)

The hydrolysis of compound 8 (n=10) was realized as described for tetrahydropyranyl ethers 8 (n=3) (vide supra) with the following quantities: tetrahydropyranyl ethers 3

(n=10) (100 mg, 0.14 mmol), oxalic acid (2 ml, 2% aqueous), ethanol (7 ml). The crude material was purified by column chromatography (toluene: acetone, 96:4) to give 17β-hydroxy-17α-(12'-iodododecynyl-4-androsten-3-one) ("EM 150", 9, n=10) (63 mg, 77%) as colorless oil; IR (neat) ν max 3600–3150 (OH), 2225 (C≡C), 1660 (C=O) and 1610 (C=C) cm$^{-1}$; $^1$H-NMR 5.74 (1H,s,—C$\underline{H}$=C—), 3.19 (2H,t,J=6.96 Hz, —C$\underline{H}_2$I), 1.20 (3H,s,19-C$\underline{H}_3$), 0.88 (3H,s, 18-C$\underline{H}_3$); MS m/e (70eV): 578 (M$^+$).

17β-Hydroxy-17α-(10'-iododecynyl)-4-androsten-3-one (9, n=8)

To a solution of butyllithium (1.45 ml of a 2.5 M solution in hexane, 3.6 mmol) in dry tetrahydrofuran (THF, 20 ml) was added dropwise a solution of diprotected ethisterone 7 (400 mg, 0.91 mmol) in dry THF (7 ml) at −40° C. The reaction mixture was then allowed to stir for 1.5 h. At −35° C., a solution of 1,8-diiodooctane (1.6 g, 870 μl, 4.37 mmol) in dry THF (5 ml) was added in one portion. The cooling bath was removed and the reaction mixture was stirred at room temperature for 17 h. Then, the solution was diluted with 100 ml of ether and was washed with water (6×30 ml), dried, filtered and concentrated to yield a diasteromeric mixture of 3,3-ethylenedioxy-17β-tetrahydropyranyloxy-17α-(10'-iododecynyl)-5-androstene (8, n=8) as an oil which was directly hydrolyzed.

To a solution of the oily tetrahydropyranyl ethers in ethanol (20 ml) was added aqueous oxalic acid (3 ml, 2% aqueous). The reaction mixture was heated at reflux for 2.5 h. Then, most of the ethanol was evaporated and the residue transferred into a separatory funnel with ether (100 ml) and was washed thoroughly with water. The ethereal phase was dried, filtered and concentrated to an oil. The residue was purified by flash chromatography (toluene:acetone, 97:3) to yield the 17β-hydroxy-17α-(10'-iododecynyl)-4-androsten-3-one (9, n=8) (170 mg, 34%).

In a similar way, compounds 9 with n equals to 9, 11 and 12 were synthesized at respective yields of 30, 26 and 36% by using respectively diiodononane, diiodoundecane and diiodododecane as reagents.

Efficacy of Compounds Synthesized in Accordance with Example 2

Figure 3:
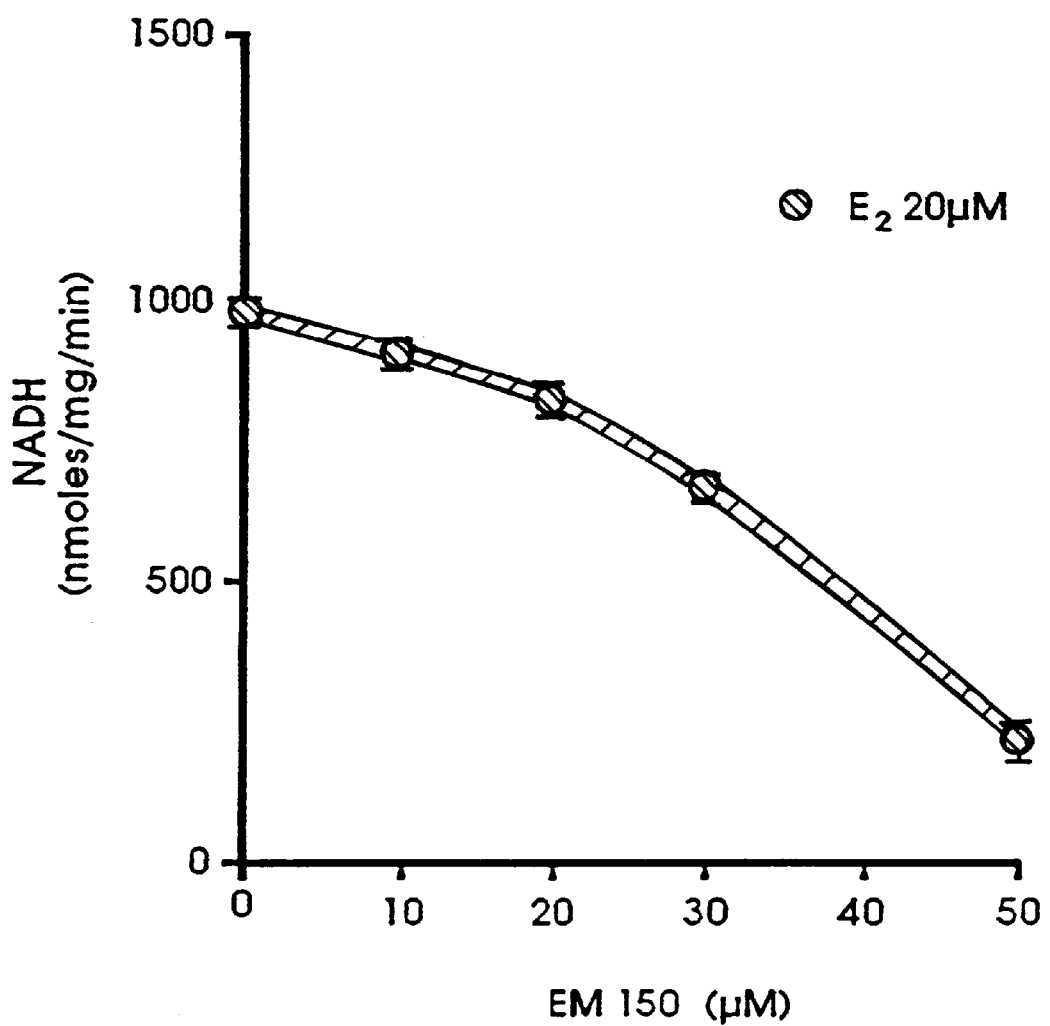
FIG. 3 is a graph showing the inhibitory effect of different concentrations of 17β-hydroxy-17α-(12-iododecynyl)-4-androsten-3-one ("EM 150") on the activity of 17β-hydroxysteroid dehydrogenase (an enzyme which catalyses various reactions involved in sex steroid synthesis).

Compound "EM 150" synthesized above has been tested and found to be an effective inhibitor of the activity of the 17β-hydroxysteroid dehydrogenase, an enzyme which catalyzes reactions involved in the synthesis of both androgens and estrogens. In order to test this inhibition, the effect of the compound on 17β-HSD conversion of estradiol to estrone was measured. The reaction was followed by monitoring the formation of NADH at 340 nm (the rate of conversion of the cofactor NAD to NADH varies directly with the rate of estradiol conversion to estrone). The ability of compounds of the invention to inhibit this reaction is indicative of their ability to inhibit the estrogen-forming reverse reaction and various androgen-forming reactions which are also catalyzed by 17β-hydroxysteroid dehydrogenase (Thomas J. L. et al., J. Biol. Chem. 258: 11500;11504, 1983). The 17β-hydroxysteroid dehydrogenase (17β-HSD) was purified to homogeneity from human placenta. A reaction vessel was prepared containing 1 μg 17β-HSD, 5 mM NAD, 20 μM 17β-estradiol. The concentrations of the tested compound is indicated along the X-axis in FIG. 3 in 1.0 ml of a mixture of Tris-HCl (50 mM), EDTA (2 mM), NaN$_3$ (5 mM). The pH was 7.5. The reaction was allowed to proceed at 25° C. for 15 min. Formation of NADH was measured at 340 nm. As shown in FIG. 3, the compound EM 150 significantly decreases the activity of 17β-hydroxysteroid dehydrogenase.

EXAMPLE 3

Synthesis of N,N, dialkyl-ω-(17'β-hydroxy-4'-androsten-3'-on-17'-yl)-(ω-1)-alkylamide (11) (Schema 3)

Ethyl-7-(17'β-hydroxy-4'-androsten-3'-on-17'α-yl)-6-heptynoate (10, n=3,R=CH$_2$CH$_3$)

A. To a suspension of sodium hydride (55 mg (60% in mineral oil), 1.37 mmol) in dry THF (3 ml) was added dropwise diethylmalonate (274 mg, 260 μl, 1.71 mmol) at 0° C. The reaction mixture was warmed up to room temperature and was stirred 30 min. Then, this solution was added dropwise (using a seringe) to a solution of alkyl iodide 8 (n=3) (208 mg, 0.34 mmol) in THF (4 ml) and the resulting mixture was stirred at room temperature for 17 h. The reaction was diluted with ether (100 ml) and washed with water (5×30 ml), dried, filtered and concentrated to an oil. The residue was partly purified by flash chromatography (hexane: acetone, 9:1) to give 170 mg, 78% of the desired malonate contaminated with some diethylmalonate (as shown by $^1$H-NMR spectroscopy) which was used as such in the next step.

B. A solution containing the malonate (170 mg, 0.265 mmol), lithium chloride (225 mg, 5.3 mmol) and water (96 mg, 96 μl, 5.3 mmol) in dimethylformamide (DMF, 7 ml) was stirred at 155° C. for 20 h. Then, ethanol (5 ml) and oxalic acid (7 ml, 2% aqueous) were added and the resulting solution was heated at 90° C. for 2 h. The reaction mixture was diluted with ether (100 ml) and washed thoroughly with water (7×30 ml). The ethereal phase was dried, filtered and concentrated to an oil. The residue was purified by flash chromatography (hexane: acetone, 4:1) to afford ethyl-7-(17'β-hydroxy-4'-androsten-3'-on-17'α-yl)-6-heptynoate (10, n=3, R=CH$_2$CH$_3$) (57 mg, 38%) as colorless oil; IR (neat) ν max 3600–3200 (OH), 1725 (C=O,ester), 1660 (C=O,enone) and 1610 (C=C) cm$^{-1}$; $^1$-NMR 5.73 (1H, s,—C$\underline{H}$=C—), 4.11 (2H,q,J=6.96 Hz, —OC$\underline{H}_2$CH$_3$), 1.24 (3H,t, J=6,96 Hz,—OC$\underline{H}_2$CH$_3$), 1.20 (3H,s,19-C$\underline{H}_3$), 0.88 (3H,s,18-C$\underline{H}_3$); MS m/e (70 eV): 440 (M$^+$).

Ethyl-10-(17'β-hydroxy-4'-androsten-3'-on-17'α-yl)-9-decynoate (10, n=6, R=CH$_2$CH$_3$)

The preparation of this ester was realized as described for ester 10 (n=3) (vide supra) with the following quantities: A. alkyl iodide 8 (n=6) (130 mg, 0.2 mmol), sodium hydride (30 mg (60% in mineral oil, 0.75 mmol), diethylmalonate (132 mg, 125 μl, 0.82 mmol), THF (7 ml), 25° C., 12 h. The crude material was used as such in part B; B. crude malonate (0,2 mmol), lithium chloride (100 mg, 2.36 mmol), water (23 mg, 23 μl, 1.27 mmol), DMF (7 ml), 155° C., 20 h; and ethanol (5 ml), oxalic acid (7ml, 2% aqueous), 90° C., 2h. The crude material was purified by preparative TLC (hexane: acetone, 4:1, Rf 0.25) to give ethyl-10-(17'β-hydroxy-4'-androsten-3'-on-17'α-yl)-9-decynoate (10, n=6, R=CH$_2$CH$_3$) (23 mg, 24%) as colorless oil; IR (neat) ν max 3650–3150 (OH), 2220 (C≡C), 1722 (C=O,ester), 1660 (C=C,enone) and 1610 (C=C) cm$^{-1}$; $^1$H-NMR 5.75 (1H, s,—C$\underline{H}$=C—), 4.13 (2H,q,J=7.32 Hz, —OC$\underline{H}_2$CH$_3$), 1.26 (3H,t,J=7.32 Hz,—OCH$_2$C$\underline{H}_3$), 1.21 (3H,s,19-C$\underline{H}_3$), 0.89 (3H,s,18-CH$_3$); MS m/e (70eV): 482 (M$^+$) along with 11 mg, 10% of the corresponding malonate (Rf 0.2).

Methyl-14-(17'β-hydroxy-4'-androsten-3'-on-17'α-yl)-13-tetradecynoate (10, n=10, R=CH$_2$CH$_3$)

The preparation of this ester was done as described for ester 10 (n=3) (vide supra) with the following quantities: A. alkyl iodide 8 (n=10) (150 mg, 0.21 mmol), sodium hydride (34 mg (60% in mineral oil), 0,85 mmol), dimethylmalonate (127 mg, 110 μl, 1 mmol), THF (10 ml), 25° C., 18 h; B. crude malonate (0,21 mmol), lithium chloride (182 mg, 4.3 mmol), water (77 mg, 77 μl, 4.3 mmol), DMF (7 ml), 155°

C., 20 h; and ethanol (5 ml), oxalic acid (7 ml, 2% aqueous), 90° C., 2 h. The crude material was purified by flash chromatography (hexane: acetone, 85:15) to give methyl-14-(17'β-hydroxy-4'-androsten-3'-on-17'α-yl)-13-tetradecynoate (10, n=10, R=CH$_2$CH$_3$) (47 mg, 42%) as colorless oil; IR (neat) ν max 3650–3150 (OH), 2225 (C≡C), 1730 (C=O,ester), 1665 (C=O,enone) and 1610 (C=C) cm$^{-1}$; $^1$H-NMR 5.74 (1H,s,—C$\underline{H}$=C—), 3.67 (3H, s,—OC$\underline{H}_3$), 1.20 (3H,s, 19-C$\underline{H}_3$), 0.88 (3H,s,18-C$\underline{H}_3$); MS m/e (70eV): 524 (M$^+$).

N-butyl-N-methyl-7-(17'β-hydroxy-4'-androsten-3'-ON-17'α-yl)-6-heptynamide (11, n=3)

A. The ethyl ester 10 (n=3, R=CH$_2$CH$_3$) (30 mg, 6.8×10$^{-2}$ mmol) was dissolved in dry ethanol (3 ml), anhydrous potassium carbonate (20 mg, 0.144 mmol) was added and the resulting solution allowed to stir under argon at room temperature overnight (16 h). The ethanol was evaporated, ether (20 ml) and water (5 ml) were added, and the mixture separated into neutral and alkali soluble fractions. The alkaline fraction was brought to pH2 with hydrochloric acid and extracted with ether (3×5 ml). The combined ethereal phases were washed with water (3×10 ml), dried, filtered and concentrated to give the crude acid which was immediately converted to the amide.

B. A solution of crude acid (6.8×10$^{-2}$ mmol) in dry dichloromethane (5 ml) was treated with tributylamine (37.3 mg, 48 μl, 0.2 mmol) and isobutyl chloroformate (27.4 mg, 26μl, 0.2 mmol) at 0° C. for 50 min. Then, N-methylbutylamine (35.3 mg, 48 μl, 0.4 mmol) was added and the mixture was stirred at 0° C. for 50 min. The reaction mixture was diluted with ether (10 ml) and was washed successively with a solution of hydrochloric acid (2×5 ml, 1% aqueous) and with water (5×5 ml). The organic phase was dried, filtered and concentrated to an oil. The residue was purified by preparative TLC (benzene: acetone, 9:1, Rf 0.08) to give N-butyl-N-methyl-7-(17'β-hydroxy-4'-androsten-3'-on-17'α-yl)-6-heptynamide (11, n=3) (15 mg, 46%) as colorless oil; IR (neat) ν max 3550–3200 (OH), 2220 (C≡C), 1660 (C=O,enone) and 1635 (C=O,amide) cm$^{-1}$; $^1$H-NMR 5.74 (1H,s, —C$\underline{H}$=C—), 3.35 and 3.25 (2H,2t,J=7.32 Hz,—NC$\underline{H}_2$—), 2.96 and 2.90 (3H,2s, —NC$\underline{H}_3$), 1.20 (3H,s,19-C$\underline{H}_3$), 0.95 (3H,t,J=6,6 Hz,-C$\underline{H}_2$C$\underline{H}_3$), 0.88 (3H,s 18-CH$_3$); MS m/e (70eV):

N-butyl-N-methyl-10-(17'β-hydroxy-4'-androsten-3'-on-17'α-yl)-decynamide (11, n=6)

The preparation of this amide was done as described for amide 11 (n=3) (vide supra) with the following quantities: A. ester 10 (n=6) (16.5 mg, 3.4×10$^{-2}$ mmol), potassium carbonate (10 mg, 7.2×10$^{-2}$ mmol), methanol (2 ml), room temperature, 2 h. The crude material was used as such in part B; B. crude acid (3.4×10$^{-2}$ mmol), tributylamine (14 mg, 18 μl, 7.5×10$^{-2}$ mmol), isobutyl chloroformate (10.5 mg, 10 μl, 7.7×10$^{-2}$ mmol), dichloromethane (3 ml), 0° C., 30 min.; N-methylbutylamine (14.7 mg, 20 μl, 0.168 mmol), 0° C., 50 min. The residue was purified by preparation TLC (hexane: acetone, 7:3, Rf 0.12) to give N-butyl-N-methyl-10-(17'β-hydroxy-4'-androsten-3'-on-17'α-yl)-9-decynamide (11, n=6) (9.3 mg, 52%) as colorless oil; IR (neat) ν max 3600–3150 (OH), 2220 (C≡C), 1660(C=O,enone) and 1630 (C=O,amide) cm$^{-1}$; $^1$H-NMR 5.73 (1H,s, —C$\underline{H}$=C—), 3.35 and 3.25 (2H,2t,J=7.32 Hz,—NC$\underline{H}_2$—), 2.96 and 2.90 (3H,2s,NC$\underline{H}_3$), 1.20 (3H,s,19-C$\underline{H}_3$), 0.95 (3H,t,J= 6,96 Hz,—CH$_2$C$\underline{H}_3$), 0.88 (3H,s,18-C$\underline{H}_3$); MS m/e (70 eV): 523 (M$^+$) and the corresponding methyl ester (6.4 mg, 40%, Rf 0.22).

N-butyl-N-methyl-14-(17'β-hydroxy-4'-androsten-3'-on-17'α-yl)-13-tetradecynamide (11, n=10)

A. To a solution of ester 10 (n=10) (24 mg, 4.58×10$^{-2}$ mmol) in methanol (5 ml) was added sodium hydroxide (0.5 ml, 5% aqueous). The reaction mixture was stirred at room temperature for 45 min. Then, ether (30 ml) was added and the resulting solution was washed successively with hydrochloric acid (2×5 ml, 10% aqueous) and with water (4×10 ml). The ethereal phase was dried, filtered and concentrated to an oil. The residue was purified by preparative TLC (hexane: acetone, 7:3, Rf 0.24) to give 5.6 mg, 24% of acid. B. The preparation of the title amide was realized as described for amide 11 (n=3) (vide supra) with the following quantities: acid (5.6 mg, 1.1×10$^{-2}$ mmol), tributylamine (14 mg, 18 μl, 7.5×10$^{-2}$ mmol), isobutyl chloroformate (10.4 mg, 10 μl, 7.7×10$^{-2}$ mmol), dichloromethane (3 ml), 0° C., 30 min.; N-methylbutylamine (14.7 mg, 20 μl, 0.168 mmol), 0° C., 50 min. The residue was purified by preparative TLC (hexane: acetone, 7:3, Rf 0.35) to give N-butyl-N-methyl-14-(17'β-hydroxy-4'-androsten-3'-on-17'α-yl)-13-tetradecynamide (11, n=10) (5.2 mg, 82%) as colorless oil; IR (neat) ν max 3600–3100 (OH), 2220 (C≡C), 1660 (C=O,enone) and 1630 (C=O,amide) cm$^{-1}$; $^1$H-NMR 5.74 (1H,s,—C$\underline{H}$=C—), 3.36 and 3.26 (2H,2t,J=7.32 Hz,—NC$\underline{H}_2$—), 2.97 and 2.91 (3H,2s,—NC$\underline{H}_3$), 1.20 (3H,s,18-C$\underline{H}_3$), 0.95 (3H,t,J=6,77 Hz,—CH$_2$C$\underline{H}_3$), 0.88 (3H,s, 19-CH$_3$); MS m/e (70eV): 579 (M$^+$).

By analogous methods to those described and using the same ester starting material, the following syntheses are performed with rent amines, and resulting compounds are summarized in Table 2.

TABLE 2

N,N'-dialkyl-ω-(17'β-hydroxy-4'-androsten-3'-on-17'α-yl)-(ω-1)-alkylamide 11

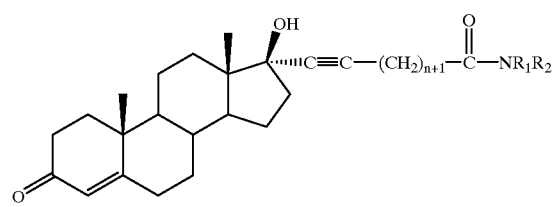

| n | R$_1$ | R$_2$ |
|---|---|---|
| 3 | methyl | n-butyl |
| 3 | H | n-butyl |
| 3 | methyl | 1H,1H-heptafluorobutyl |
| 6 | methyl | n-butyl |
| 6 | H | n-butyl |
| 6 | methyl | 1H,1H-heptafluorobutyl |
| 10 | methyl | n-butyl |
| 10 | H | n-butyl |
| 10 | methyl | 1H,1H-heptafluorobutyl |

SCHEME 3

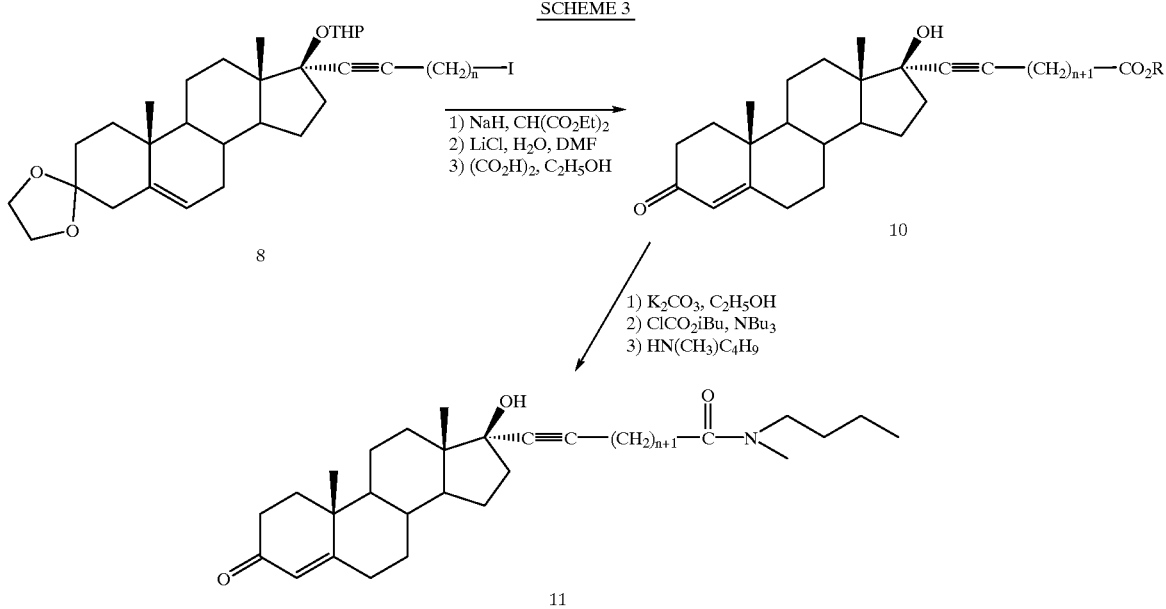

What is claimed is:

1. A compound represented by the formula:

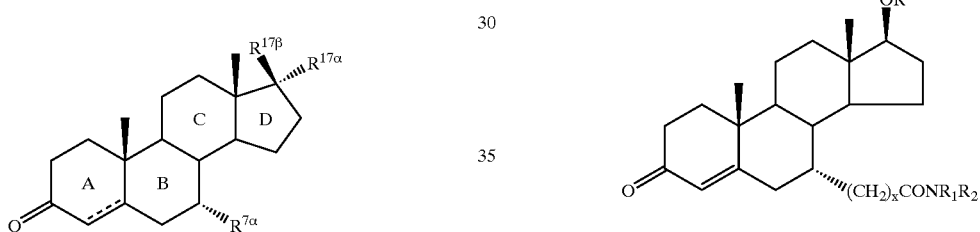

wherein the dotted line represents an optional pi bond, and (i) $R^{7\alpha}$ is $(CH_2)_y L$—G wherein y is an integer from 4–20, L is selected from the group consisting of —$CONR^4$—, —$CSNR^4$—, —$NR^5CS$— or —$CH_2$— ($R^4$ and $R^5$ being H or methyl), and G is selected from the group consisting of lower alkyl, lower alkenyl and halo ($C_1$–$C_8$) alkyl, $R^{17\beta}$ is hydroxyl or alkanoyloxy, and $R^{17\alpha}$ is hydrogen, ($C_1$–$C_8$) alkyl, or $R^{17\beta}$ and $R^{17\alpha}$ together are represented by the formula

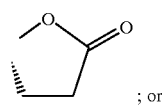 ; or (ii) $R^{17\alpha}$ is —C≡C—$(CH_2)_y$—L—G, wherein y is an integer from 4–20, L is selected from the group consisting of —$CONR^4$—, —$CSNR^4$—, —$NR^5CS$— or —$CH_2$— ($R^4$ and $R^5$ being H or methyl), and G is selected from the group consisting lower alkyl, lower alkenyl and haloalkyl, $R^{17\beta}$ is a hydroxyl group or an ester derivative thereof, $R^{7\alpha}$ is hydrogen.

2. Compounds according to claim 1, represented by the formula:

said compounds being selected from the following group:

| x  | R                           | $R_1$  | $R_2$                |
|----|-----------------------------|--------|----------------------|
| 14 | H                           | methyl | n-butyl              |
| 14 | $CH_3CO$                    | methyl | n-butyl              |
| 12 | H                           | methyl | n-butyl              |
| 12 | $CH_3CO$                    | methyl | n-butyl              |
| 10 | H                           | H      | n-butyl              |
| 10 | H                           | methyl | 1H,1H-heptafluorobutyl |
| 10 | H                           | methyl | n-pentyl             |
| 10 | $CH_3CO$                    | methyl | n-butyl              |
| 10 | $C_2H_5CO$                  | methyl | n-butyl              |
| 10 | trans-4-n-butyl cyclo $C_6H_{10}CO$ | methyl | n-butyl      |
| 10 | cyclo $C_5H_9$—$CH_2CO$     | methyl | n-butyl              |
| 8  | H                           | H      | n-butyl              |
| 8  | H                           | methyl | n-butyl              |
| 8  | $CH_3CO$                    | methyl | n-butyl              |
| 6  | H                           | methyl | n-butyl              |
| 6  | $CH_3CO$                    | methyl | n-butyl              |
| 10 | H                           | methyl | n-butyl              |

3. A compound represented by the formula:

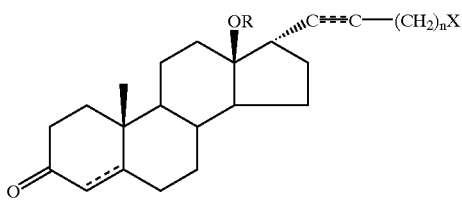

wherein the dotted lines represent optional carbon-carbon bonds;

n is an integer from 1–14;

R is selected from the group consisting of hydrogen, $(C_1-C_8)$ alkyl, $(C_1-C_{20})$ alkanoyl, $(C_3-C_{20})$ alkenoyl, $(C_3-C_{20})$ alkynoyl, $(C_7-C_{11})$ aryl and alkylsilyl; and X is selected from the group consisting of halogen, —CN, a 3–9 membered nitrogen hetero ring and $N(R^7)_2$ ($R^7$ being hydrogen or $(C_1-C_8)$ alkyl).

4. A compound according to claim 3 represented by the formula:

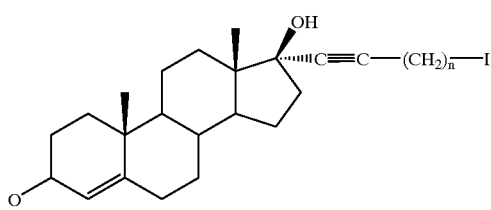

wherein n is an integer from 1 to 14.

5. Compounds according to claim 1 represented by the formula:

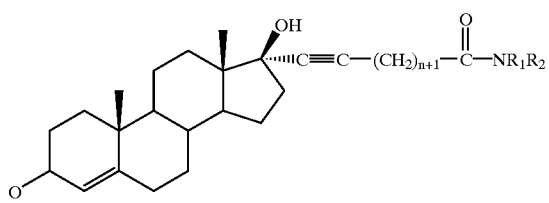

said compounds being selected from the following group:

| n | $R_1$ | $R_2$ |
|---|---|---|
| 3 | methyl | n-butyl |
| 3 | H | n-butyl |
| 3 | methyl | 1H,1H-heptafluorobutyl |
| 6 | methyl | n-butyl |
| 6 | H | n-butyl |
| 6 | methyl | 1H,1H-heptafluorobutyl |
| 10 | methyl | n-butyl |

-continued

| n | $R_1$ | $R_2$ |
|---|---|---|
| 10 | H | n-butyl |
| 10 | methyl | 1H,1H-heptafluorobutyl. |

6. A compound selected from the group consisting of N-butyl, N-methyl-11-(17'β-hydroxy-4'-androsten-3'-on-7'α-yl) undecanamide, 17β-hydroxy-17α-(12'-iodododecynyl)-4-androsten-3-one, and 17β-hydroxy-17α-(5'-iodopentynyl)-4-androsten-3-one.

7. A pharmaceutical composition comprising a pharmaceutically acceptable diluent or carrier and a therapeutically effective amount of at least one compound of claim 1.

8. A pharmaceutical composition comprising a pharmaceutically acceptable diluent or carrier and a therapeutically effective amount of at least one compound of claim 3.

9. A pharmaceutical composition comprising a pharmaceutically acceptable diluent or carrier and a therapeutically effective amount of at least one compound according to claim 6.

10. A method of treating prostate cancer comprising administering to a patient in need of such treatment a therapeutically effective amount of at least one compound according to claim 1.

11. A method of treating prostate cancer comprising administering to a patient in need of such treatment a therapeutically effective amount of at least one compound according to claim 3.

12. A method of treating prostate cancer comprising administering to a patient in need of such treatment a therapeutically effective amount of at least one compound according to claim 6.

13. A method for treating benign prostatic hyperplasia comprising administering to a patient in need of such treatment a therapeutically effective amount of at least one compound according to claim 1.

14. A method for treating benign prostatic hyperplasia comprising administering to a patient in need of such treatment a therapeutically effective amount of at least one compound according to claim 3.

15. A method for treating benign prostatic hyperplasia comprising administering to a patient in need of such treatment a therapeutically effective amount of at least one compound according to claim 6.

16. A method for treating an androgen-related disease in a patient in need of such treatment comprising administering to said patient a therapeutically effective amount of at least one compound according to claim 1.

17. A method for treating an androgen-related disease in a patient in need of such treatment comprising administering to said patient a therapeutically effective amount of at least one compound according to claim 3.

18. A method for treating an androgen-related disease in a patient in need of such treatment comprising administering to said patient a therapeutically effective amount of at least one compound according to claim 6.

* * * * *